US010724000B2

(12) United States Patent
Graf et al.

(10) Patent No.: US 10,724,000 B2
(45) Date of Patent: Jul. 28, 2020

(54) SMALL MOLECULE BASED CONVERSION OF SOMATIC CELLS INTO NEURAL CREST CELLS

(71) Applicant: Hoffmann-La Roche Inc., Little Falls, NJ (US)

(72) Inventors: Martin Graf, Gelterkinden (CH); Roberto Iacone, Basel (CH); Eva Christina Thoma, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 15/004,745

(22) Filed: Jan. 22, 2016

(65) Prior Publication Data

US 2016/0369233 A1 Dec. 22, 2016

Related U.S. Application Data

(63) Continuation of application No. PCT/EP2014/065460, filed on Jul. 18, 2014.

(30) Foreign Application Priority Data

Jul. 23, 2013 (EP) ..................... 13177606

(51) Int. Cl.
*C12N 5/0797* (2010.01)
*A61K 35/30* (2015.01)

(52) U.S. Cl.
CPC ............. *C12N 5/0623* (2013.01); *A61K 35/30* (2013.01); *C12N 2500/90* (2013.01); *C12N 2501/15* (2013.01); *C12N 2501/155* (2013.01); *C12N 2501/727* (2013.01); *C12N 2501/999* (2013.01); *C12N 2506/1307* (2013.01)

(58) Field of Classification Search
CPC ............ C12N 5/0623; C12N 2501/999; C12N 2500/90; C12N 2506/1307; C12N 2501/727; C12N 2501/155; C12N 2501/15; A61K 35/30; A61P 25/00; A61P 21/00; A61P 19/00
See application file for complete search history.

(56) References Cited

U.S. PATENT DOCUMENTS

2012/0021519 A1* 1/2012 Ichida et al. ........... C12N 5/071
435/377

FOREIGN PATENT DOCUMENTS

| WO | 03/076429 A2 | 9/2003 |
| WO | 2010/108126 A2 | 9/2010 |
| WO | 2012/006577 A2 | 1/2012 |
| WO | 2012/022725 A2 | 2/2012 |
| WO | 2012/087965 A2 | 6/2012 |

OTHER PUBLICATIONS

Menendez et al. Wnt signaling and a Smad pathway blockade direct the differentiation of human pluripotent stem cells to multipotent neural crest cells. PNAS 2011. vol. 108, No. 48: p. 19240-19245 (Year: 2011).*
Huangfu et al. Induction of pluripotent stem cells from primary human fibroblasts with only Oct4 and Sox2. Nature Biotechnology. vol. 26, No. 11, 2008, p. 1269-1275 (Year: 2008).*
Kim et al. Generation of Human Induced Pluripotent Stem Cells by Direct Delivery of Reprogramming Proteins. Cell Stem Cell 4, 2009, p. 472-476 (Year: 2009).*
Dalton. Signaling networks in human pluripotent stem cells. Curr Opin Cell Biol. Apr. 2013 ; 25(2): 241-246 (Year: 2013).*
Gong et al. Discovery of potent and bioavailable GSK-3b inhibitors. Bioorganic & Medicinal Chemistry Letters 20 (2010) 1693-1696 (Year: 2010).*
Wang et al. Induced Pluripotent Stem Cells for Neural Tissue Engineering. Biomaterials. Aug. 2011 ; 32(22): 5023-5032. (Year: 2011).*
Liu et al. Human Neural Crest Stem Cells Derived from Human ESCs and Induced Pluripotent Stem Cells: Induction, Maintenance, and Differentiation into Functional Schwann Cells. Stem Cells Translationalmedicine 2012;1:266-278 (Year: 2012).*
Zhang et al. Small molecules, big roles—the chemical manipulation of stem cell fate and somatic cell reprogramming. Journal of Cell Science 125 (23), p. 5609-5620 (Year: 2012).*
International Search Report and the Written Opinion dated Oct. 16, 2014, for PCT Patent Application No. PCT/EP2014/065460 filed on Jul. 18, 2014, thirteen pages.
International Preliminary Report on Patentability dated Feb. 4, 2016, for PCT Patent Application No. PCT/EP2014/065460 filed on Jul. 18, 2014, eight pages.
Alexanian et al., (2013). "Enhancing the efficiency of direct reprogramming of human mesenchymal stem cells into mature neuronal-like cells with the combination of small molecule modulators of chromatin modifying enzymes, SMAD signaling and cyclic adenosine monophosphate levels," *The International Journal of Biochemistry & Cell Biology* 45:1633-1638.
Breitenlechner et al., (2004). "Structure-Based Optimization of Novel Azepane Derivatives as PKB Inhibitors," *Journal of Medicinal Chemistry* 47(6):1375-1390.
Ladewig et al., (2013). "Leveling Waddington: the emergence of direct programming and the loss of cell fate hierarchies," *Molecular Cell Biology* 14:225-236.
Ma et al., (2013). "Progress in the Reprogramming of Somatic Cells," *Circulation Research* 112:562-574.
Zhu et al., (2012). "Direct Conversion of Porcine Embryonic Fibroblasts into Adipocytes by Chemical Molecules," *Cellular Reprogramming* 14(2):99-105.
Bhatheja et al., "Schwann cells: Origins and role in axonal maintenance and regeneration" The International Journal of Biochemistry & Cell Biology 38:1995-1999 (2006).

(Continued)

*Primary Examiner* — Taeyoon Kim
(74) *Attorney, Agent, or Firm* — Hoffmann-La Roche Inc.; Jonathan P. Aumais

(57) ABSTRACT

This application relates to a method for differentiating somatic cells into multi-competent neural crest cells based on linked steps of chemically defined medium inductions. Neural crest cells are able to differentiate into numerous cell types like Schwann cells, chondrocytes, smooth muscle cells or adipocytes.

10 Claims, 20 Drawing Sheets

(56) References Cited

OTHER PUBLICATIONS

Figure 1A:
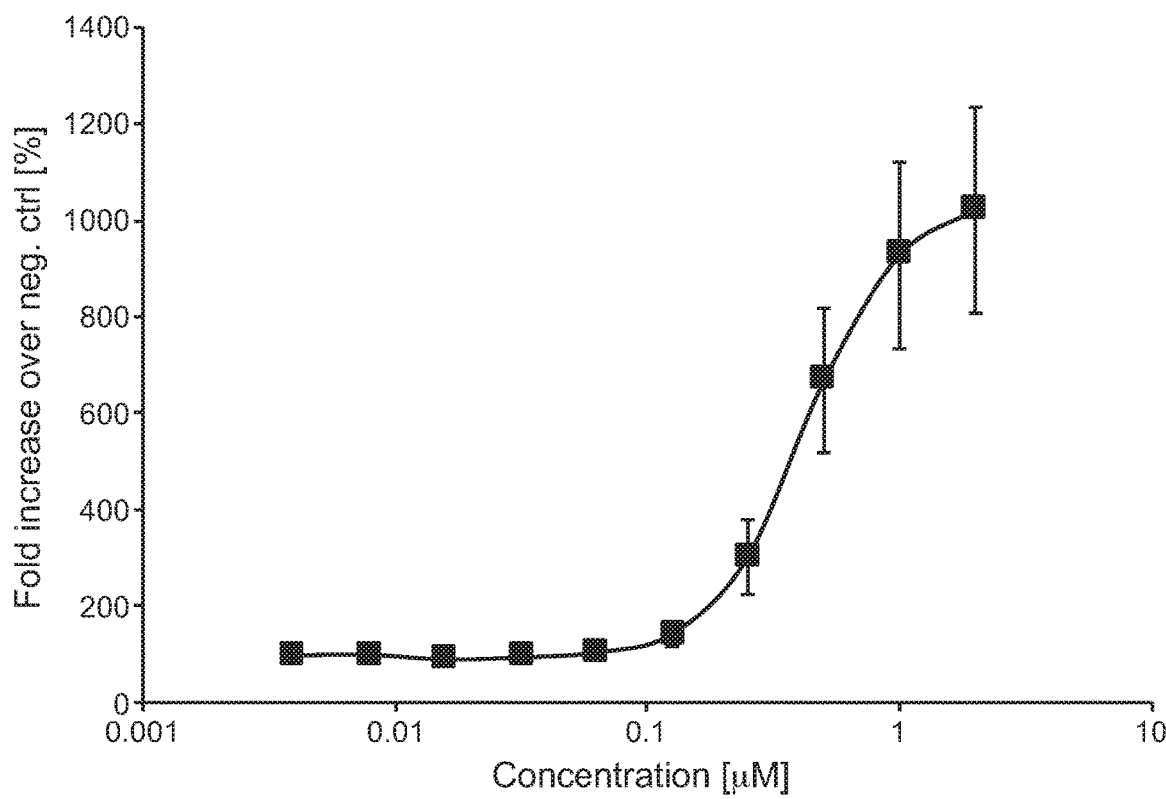

Bronner-Fraser et al., "An Antibody to a Receptor for Fibronectin and Laminin Perturbs Cranial Neural Crest Development in Vivo" Development Biology 117:528-536 (1986).
Casella et al., "Improved Method for Harvesting Human Schwann Cells From Mature Peripheral Nerve and Expansion In Vitro" Glia 17:327-338 (1996).
Chambers et al., "Highly efficient neural conversion of human ES and iPS cells by dual inhibition of SMAD signaling" Nature Biotechnology 27:275-280 (2009).
Chung et al., "Stem Cell Property of Postmigratory Cranial Neural Crest Cells and Their Utility in Alveolar Bone Regeneration and Tooth Development" Stem Cells 27:866-877 (2009).
Desban et al., "alpha1beta1-integrin engagement to distinct laminin-1 domains orchestrates spreading, migration and survival of neural crest cells through independent signaling pathways" Journal of Cell Science 119:3206-3218 (2006).
Ding et al., "Rho kinase inhibitor Fasudil induces neuroprotection and neurogenesis partially through astrocyte-derived G-CSF" Brain, Behavior, and Immunity 23:1083-1088 (2009).
Dontu et al., "In vitro propagation and transcriptional profiling of human mammary stem/progenitor cells" Genes & Development 17:1253-1270 (2003).
Fernandes et al., "A dermal niche for multipotent adult skin-derived precursor cells" Nature Cell Biology 6:1082-1093 (2004).
Groysman et al., "A negative modulatory role for rho and rho-associated kinase signaling in delamination of neural crest cells" Neural Development 3(27) (2008).
Hunt et al., "A Highly Enriched Niche of Precursor Cells with Neuronal and Glial Potential Within the Hair Follicle Dermal Papilla of Adult Skin" Stem Cells 26:163-172 (2008).
John et al., "Transforming Growth Factor beta-Mediated Sox10 Suppression Controls Mesenchymal Progenitor Generation in Neural Crest Stem Cells" Stem Cells 29:689-699 (2011).
Ladewig et al., "S mall molecules enable highly efficient neuronal conversion of human fibroblasts" Nature Methods 9(6):575-578 (2012).
Li et al., "Concise Review: A Chemical Approach to Control Cell Fate and Function" 30:61-68 (2012).
Liu et al., "ROCK Inhibitor and Feeder Cells Induce the Conditional Reprogramming of Epithelial Cells" The American Journal of Pathology 180(2):599-607 (2012).
McKenzie et al., "Skin-Derived Precursors Generate Myelinating Schwann Cells for the Injured and Dysmyelinated Nervous System" The Journal of Neuroscience 26(24):6651-6660.
Okita et al., "Generation of germline-competent induced pluripotent stem cells" Nature 448:313-317 (2007).
Schoenebeck et al., "Sgk1, a cell survival response in neurodegenerative diseases" Molecular and Cellular Neuroscience 30:249-264 (2005).
Seaberg et al., "Clonal identification of multipotent precursors from adult mouse pancreas that generate neural and pancreatic lineages" Nature Biotechnology 22(9):1115-1124 (2004).
Shah et al., "Alternative Neural Crest Cell Fates Are Instructively Promoted by TGFbeta Superfamily Members" Cell 85:331-343 (1996).
Stuhlmiller et al., "Current perspectives of the signaling pathways directing neural crest induction" Cellular and Molecular Life Sciences 69:3715-3737 (2012).
Takahashi et al., "Induction of Pluripotent Stem Cells from Mouse Embryonic and Adult Fibroblast Cultures by Defined Factors" Cell 126:663-676 (2006).
Terunuma et al., "Efficient Procurement of Epithelial Stem Cells from Human Tissue Specimens Using a Rho-Associated Protein Kinase Inhibitor Y-27632" Tissue Engineering: Part A 16(4):1363-1368 (2010).
Toma et al., "Isolation and Characterization of Multipotent Skin-Derived Precursors from Human Skin" Stem Cells 23:727-737 (2005).
Toma et al., "Isolation of multipotent adult stem cells from the dermis of mammalian skin" Nature Cell Biology 3:778-784 (2001).
Tropepe et al., "Retinal Stem Cells in the Adult Mammalian Eye" Science 287:2032-2036 (2000).
Vazquez-Martin et al., "Activation of AMP-activated protein kinase (AMPK) provides a metabolic barrier to reprogramming somatic cells into stem cells" Cell Cycle 11(5):974-989 (2012).
Vierbuchen et al., "Direct lineage conversions: unnatural but useful?" Nature Biotechnology 29:892-907 (2011).
Watanabe et al., "A ROCK inhibitor permits survival of dissociated human embryonic stem cells" Nature Biotechnology 25:681-686 (2007).
Yu et al., "Efficient Feeder-Free Episomal Reprogramming with Small Molecules" PLoS One(6):e17557.

* cited by examiner

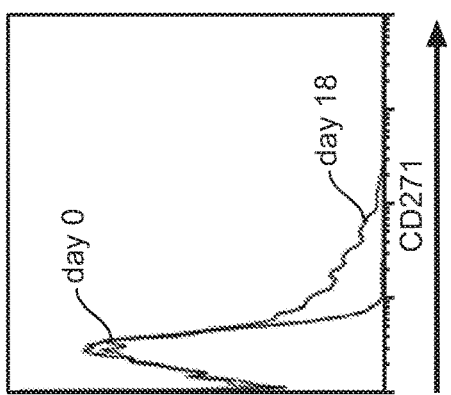
FIG. 2A
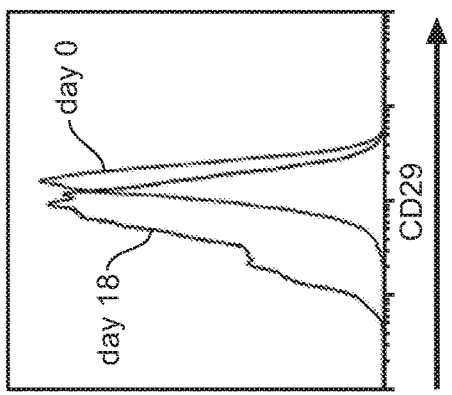
FIG. 2B
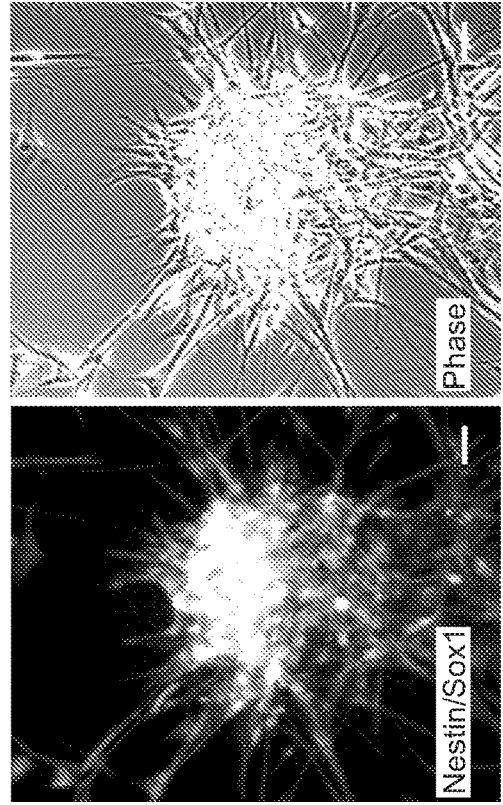
FIG. 2C
FIG. 2D
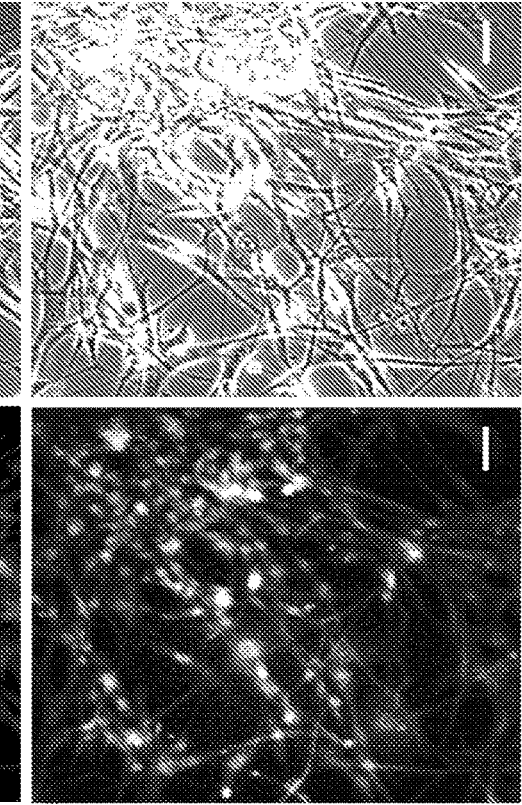
FIG. 2E

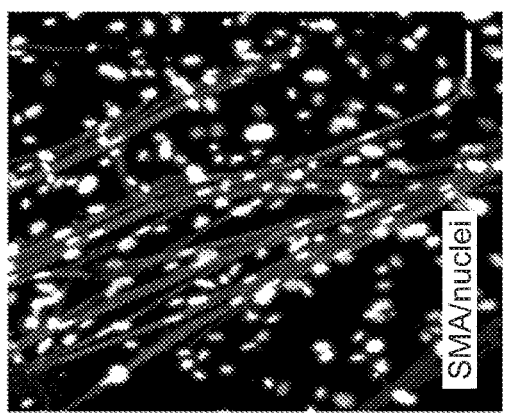
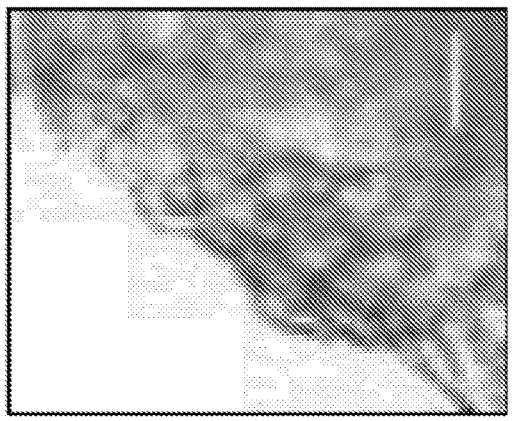
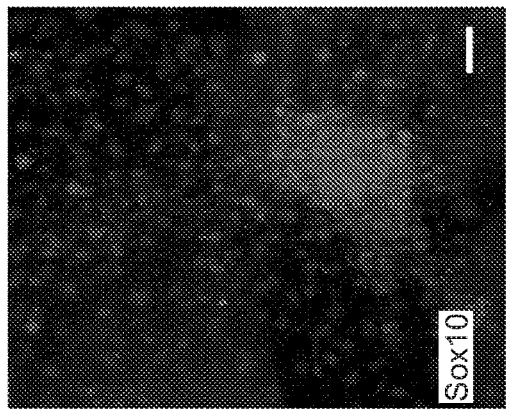
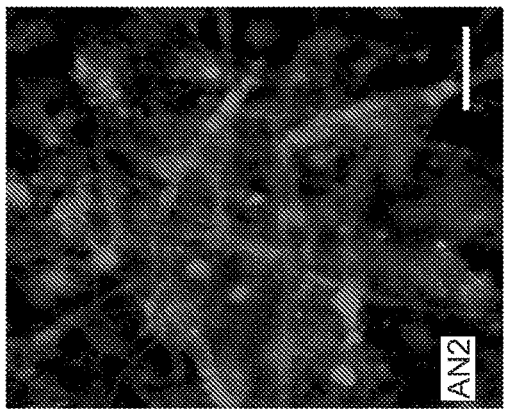
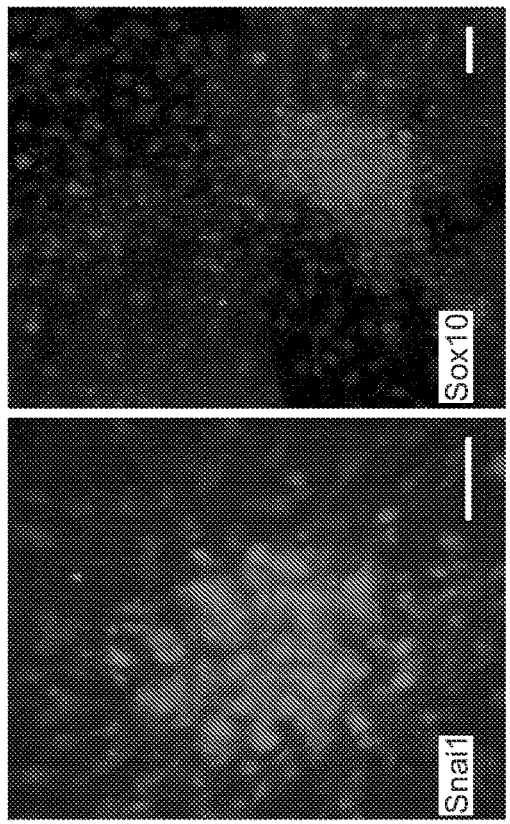
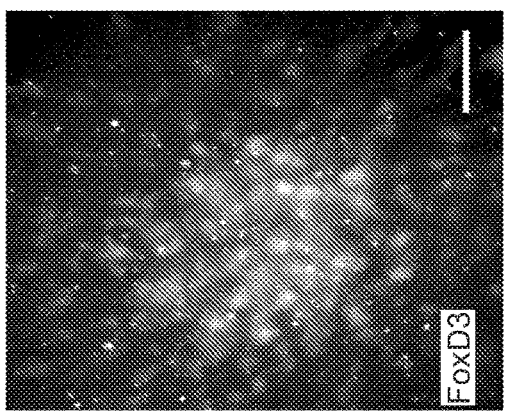

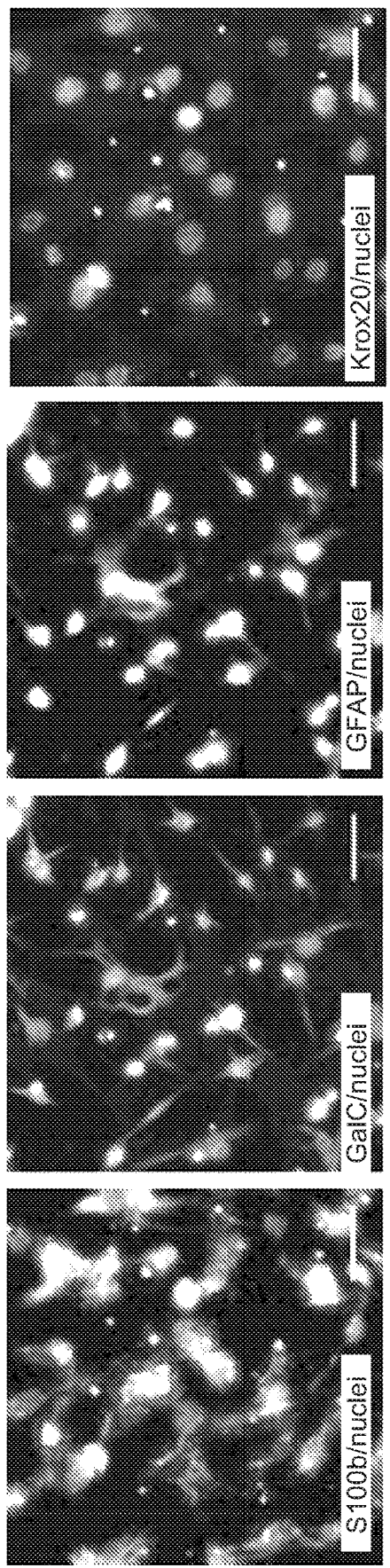
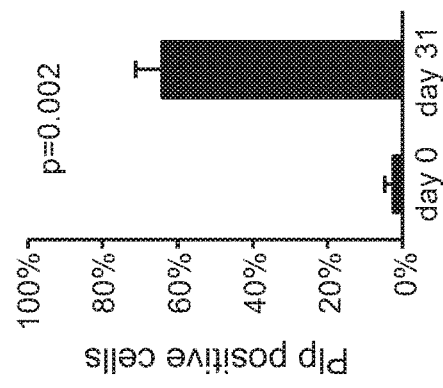
FIG. 3A  FIG. 3B  FIG. 3C  FIG. 3D  FIG. 3E

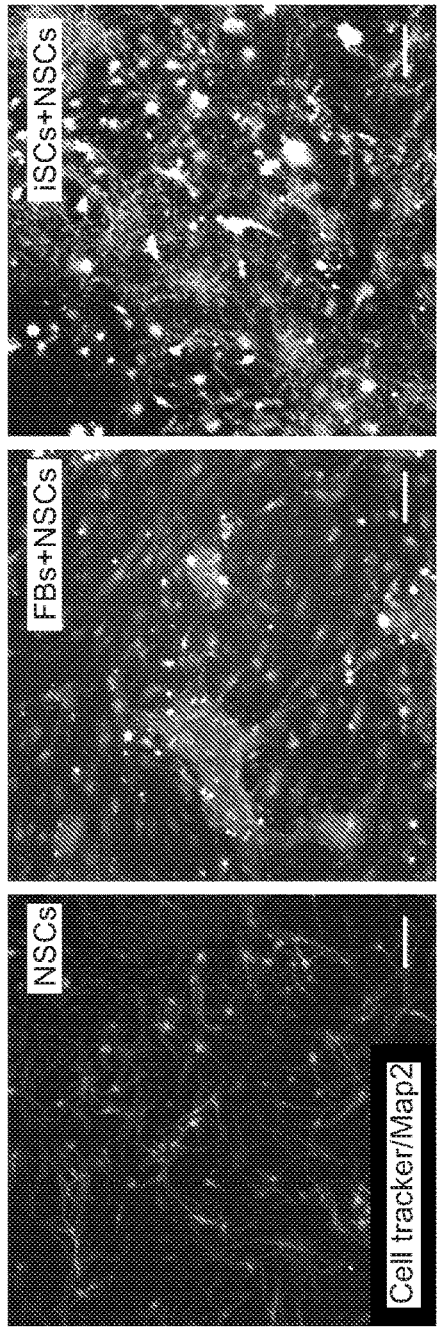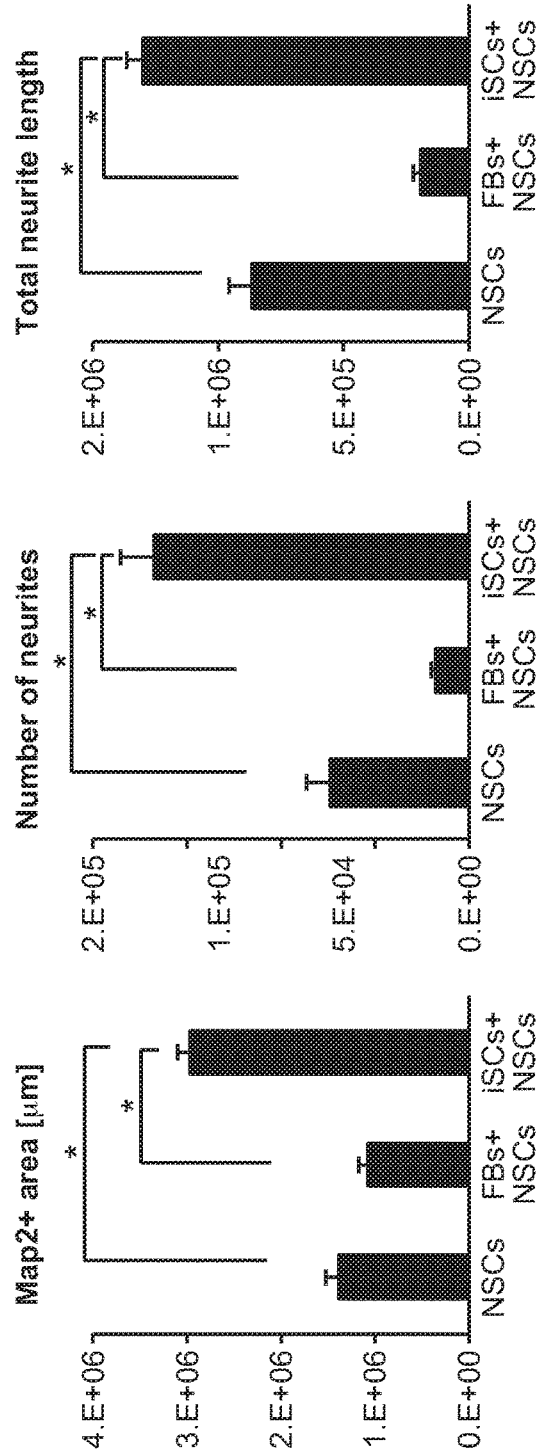

Figure 5C:
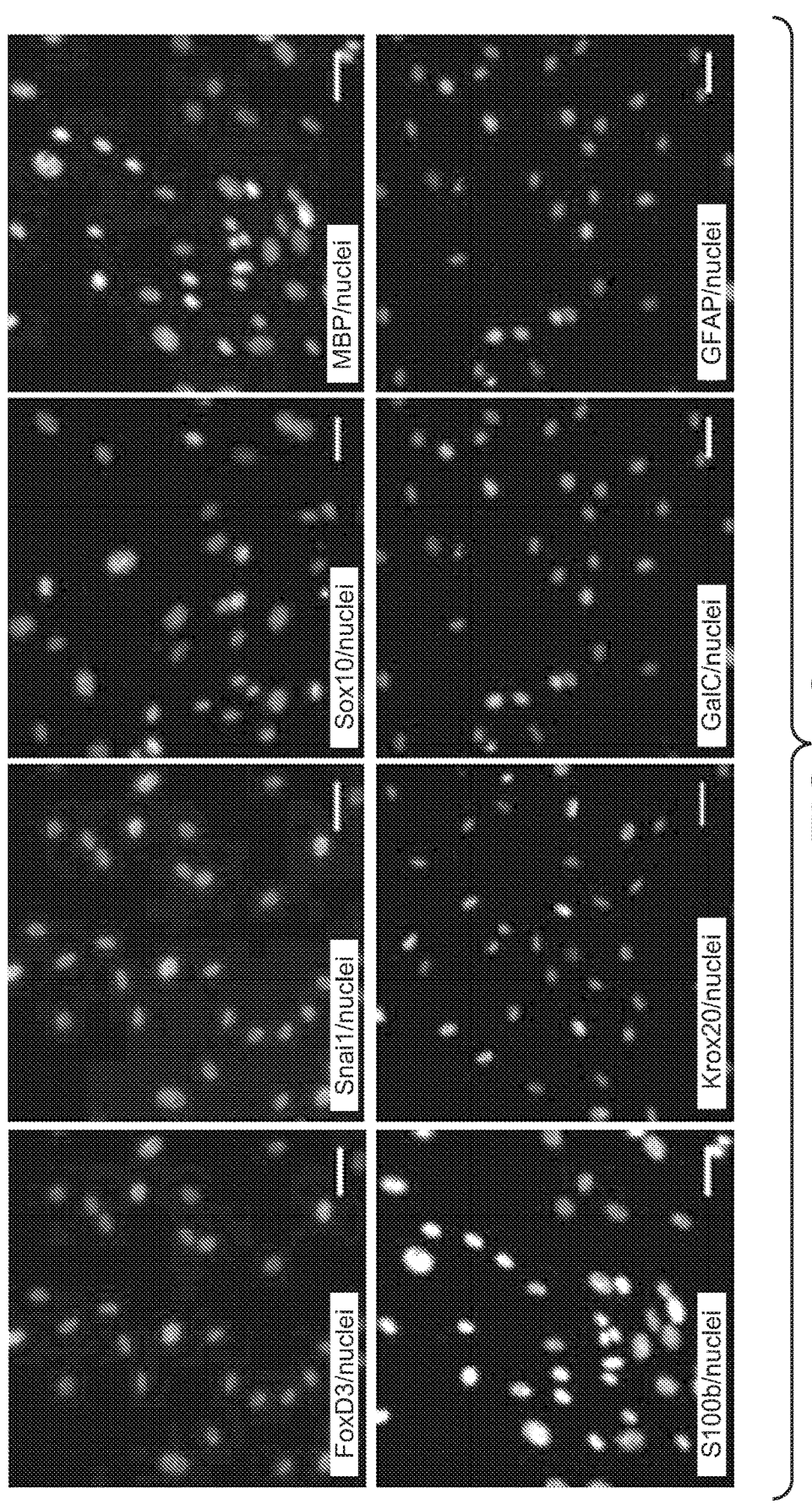

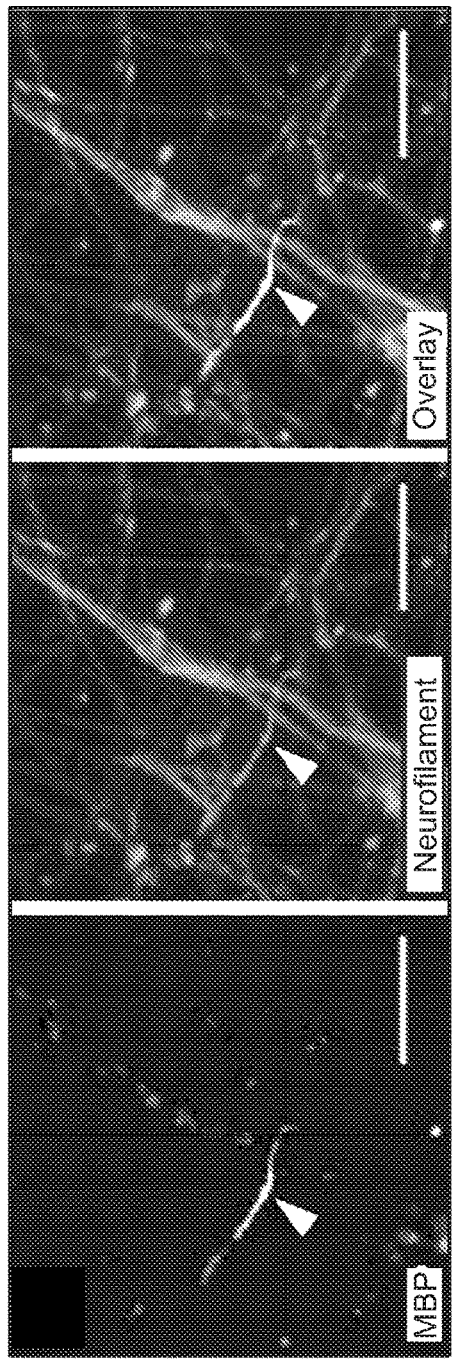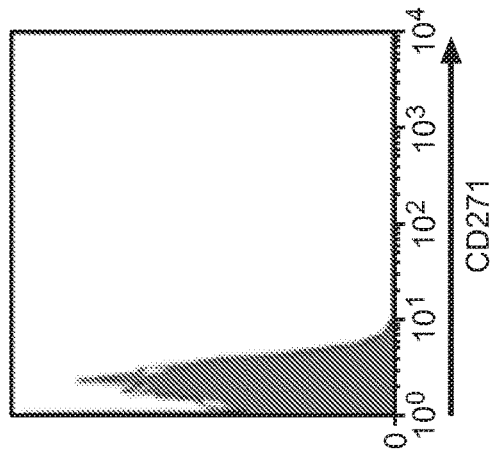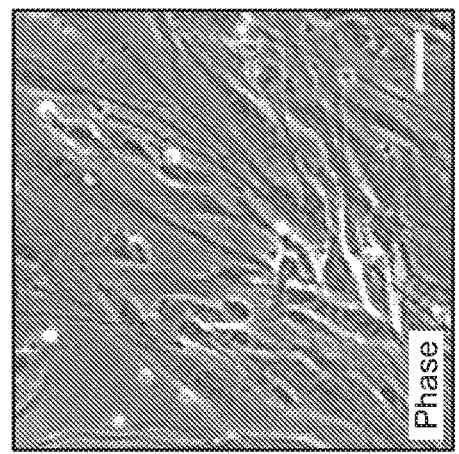
FIG. 4G
FIG. 5A
FIG. 5B

SMALL MOLECULE BASED CONVERSION OF SOMATIC CELLS INTO NEURAL CREST CELLS

CROSS REFERENCE TO RELATED APPLICATIONS

This application is a continuation of International Application No. PCT/EP2014/065460 having an international filing date of Jul. 18, 2014, the entire contents of which are incorporated herein by reference, and which claims benefit under 35 U.S.C. § 119 to European Patent Application No. 13177606.4 filed on Jul. 23, 2013.

FIELD OF THE INVENTION

This application relates to a method for differentiating somatic cells into multi-competent neural crest cells based on linked steps of chemically defined medium inductions. Neural crest cells are able to differentiate into numerous cell types like Schwann cells, chondrocytes, smooth muscle cells or adipocytes.

BACKGROUND

The Nobel-price winning method of reprogramming somatic cells into induced pluripotent stem cells by ectopic expression of four key developmental genes c-myc, Sox2, Oct4 and Klf4 is a powerful tool to obtain patient-specific pluripotent cells capable of differentiating into any cell type (Takahashi and Yamanaka, 2006). More recently, different studies have reported that cell type-specific genes can also directly convert one somatic cell type into another, a process reported as cell conversion or transdifferentiation (Vierbuchen and Wernig, 2011). This approach represents a promising strategy to obtain various defined cells for clinics and research, avoiding the potentially tumorigenic pluripotent stage.

A major drawback of known cell conversion or reprogramming strategies is the requirement of introducing ectopic genes which might have undesired effects in later applications of the converted cells. To allow for prolonged and stable expression, the ectopic genes often have to be stably integrated into the genome. Despite the possibilities to tightly control ectopic gene expression, the integrated genes may have undesired effects. For example the introduction of the proto-oncogene c-myc increased the risk of tumor formation in chimeric animals due to c-myc reactivation (Okita et al., 2007). In general, the complex regulation machinery of the genome makes it rather difficult to predict long-term effects of genetic modifications.

To avoid the disadvantages of gene integration in reprogramming approaches, novel methods replace key reprogramming genes by small molecules. Li et al generated IPS cell by replacing certain genes with small molecules that modify specific signaling pathways like Wnt or TGF-β (Li et al., 2012). Yield and efficiency of gene-mediated conversion of fibroblasts into neurons was greatly increased by small molecule based inhibition of BMP, TGF β and GSK3b signaling (Ladewig et al., 2012). In line with these results, small molecules have also been proven valuable tools for directing the differentiation of stem cells. For example, inhibition of bone morphogenetic protein (BMP) and TGF-β signaling leads to highly efficient neural induction of stem cells (Chambers et al., 2009).

The mechanisms by which small molecules influence cell fate decisions are not completely understood. While small molecules can be sufficient to induce differentiation, induction of cell conversion to pluripotency or another somatic cell type still requires ectopic gene expression. This may be due to the fact that changing a phenotype of a terminally differentiated cell into a different cell type is a non-physiological procedure compared to the differentiation of a stem cell into a somatic cell.

Provided herein is a novel method to convert somatic cells into multipotent neural crest cells, which is solely based on small molecule treatment and defined culture conditions and does not require to genetically modify the cells by the introduction of genes.

This novel method employs a novel multikinase inhibitor to transdifferentiate somatic cells into a proliferative neural crest like stage. The neural crest cells can be differentiated into multiple cell types like Schwann cells, chondrocytes, smooth muscle cells or adipocytes.

For example the differentiation of the neural crest cells into Schwann cells can be induced by a specific medium in combination with small molecule based inhibition of defined signaling pathways. The neural mature Schwann cells represent the glia cells of the peripheral nervous system (PNS). Schwann cells fulfill numerous functions like immunoprotection, nutrient supply and myelination of the neurons. Schwann cell dysfunction is the cause for many neurological disorders of the peripheral nervous system, e.g. multiple sclerosis or myelination diseases.

Importantly, this novel cell conversion method does not require the expression of any ectopic gene, but is solely based on chemical treatment. It therefore represents a promising approach to generate patient specific neural crest cells or differentiated cells like Schwann cells, chondrocytes, smooth muscle cells or adipocytes.

SUMMARY OF THE INVENTION

Provided herein is a method of Neural Crest cells from somatic cells, comprising:

a) culturing somatic cells in medium supplemented with valproic acid, b) culturing the cells obtained in step (a) in a serum-free medium supplemented with N-{(3R,4R)-4-[4-(2-Fluoro-6-hydroxy-3-methoxy-benzoyl)-benzoyl amino]-azepan-3-yl}-4-hydroxy-3,5-dimethyl-benzamide.

In one embodiment the method does not comprise genetically modifying the somatic cells or the cells obtained in step (a) by the introduction of genes.

In one embodiment step b) comprises culturing the cells in suspension culture.

In one embodiment the serum-free medium of step b) is supplemented with an inhibitor of bone morphogenetic protein (BMP). In one embodiment the inhibitor of BMP is noggin.

In one embodiment the serum-free medium of step b) is supplemented with a small molecule inhibitor of Transforming growth factor beta (TGF β).

In one embodiment the small molecule inhibitor of TGF β is SB431542.

In one embodiment the serum-free medium of step b) is supplemented with a small molecule inhibitor of glycogen synthase kinase 3 (GSK3β).

In one embodiment the inhibitor of GSK3β is 3-(3-Amino-phenyl)-4-(1-methyl-1H-indol-3-yl)-pyrrole-2,5-dione.

In one embodiment step a) comprises culturing the cells for 2 days.

In one embodiment step b) comprises culturing the cells for 7 days.

In one embodiment the somatic cells are fibroblasts.

In one embodiment the somatic cells are human cells.

In one embodiment the somatic cells are obtained from a subject suffering from a neurological disease.

In one embodiment Neural Crest cells obtained by a method according to any of the above embodiments are provided.

In one embodiment the method further comprises c) incubating the product of steps b) under conditions suitable for differentiation of the neural crest cells into a differentiated cell selected from the group of Schwann Cell, chondrocyte, smooth muscle cell or adipocyte.

In one embodiment Schwann Cells, chondrocytes, smooth muscle cells or adipocytes obtained by a method according to any of the above embodiments are provided.

In one embodiment a biobank of Neural Crest cells or differentiated Schwann Cells, chondrocytes, smooth muscle cells or adipocytes are provided.

In one embodiment the Neural Crest cells or differentiated Schwann Cells, chondrocytes, smooth muscle cells or adipocytes are used as in vitro model for neurological diseases.

One embodiment comprises a therapeutic composition comprising Neural Crest cells or differentiated Schwann Cells, chondrocytes, smooth muscle cells or adipocytes or a biobank comprising these cells.

One embodiment comprises use of N-{(3R,4R)-4-[4-(2-Fluoro-6-hydroxy-3-methoxy-benzoyl)-benzoylamino]-azepan-3-yl}-4-hydroxy-3,5-dimethyl-benzamide in a method for producing neural crest cells from somatic cells.

One embodiment comprises use of 3-(3-Amino-phenyl)-4-(1-methyl-1H-indol-3-yl)-pyrrole-2,5-dione in a method for producing neural crest cells from somatic cells.

Any of the above embodiments may be present singly or in combination.

SHORT DESCRIPTION OF THE FIGURES

FIG. 1: Identification of a small molecule enhancing neural stem cell (NSC) proliferation and enabling conversion of fibroblasts into neurosphere-like structures. A: Compound B promoted proliferation of ESC-NSCs in a dose-dependent manner. Proliferation was analysed by ATP assay and mean values of 2 experiments are shown. B: Fibroblasts treated with Compound B formed sphere-like structure in suspension culture. Scale bars: 200 µm. C: Kinase selectivity profiling of Compound B. Orange bars represent kinases that were inhibited more than 80 percent. D: Single or combined inhibition of Compound B targets by other compounds (compound targets displayed in parentheses in legend) had no or smaller effect on sphere formation of fibroblasts. Graphs show proliferation rate as fold change of initial cell number (left) and mean sphere diameter (right) at day 3 of suspension culture. Columns show mean+/−SD of three independent experiments. Data were evaluated using Student's t-test. *: $p<0.05$ compared to DMSO control. +: $p<0.05$ for Compound B compared to single inhibitors. E: Scheme of experimental setup for conversion of human fibroblasts into induced Schwann cells (iSCs).

FIG. 2: Conversion of human fibroblasts into a neural-crest like stage. A-D: Secondary spheres at day 11 of conversion with bipolar cells growing out of spheres and expressing early neural plate markers Sox1 and Nestin. Scale bars: 50 µm. E: Flow cytometry of converted neural crest cells (day 18) and fibroblasts (day 0) revealed downregulation of fibroblasts marker CD29 and upregulation of neural crest marker CD271. Lower panels show quantification of mean fluorescence intensity (MFI). Columns show mean+/−SD of three independent experiments and data were evaluated using Student's t-test. F-I: At day 18 of conversion, cells had migrated out of spheres and expressed neural crest markers Snail, Sox10, FoxD3, and AN2. Scale bars: 100 µm. J-M: Non-neural differentiation of neural crest-like cells. Cultivation in specific differentiation media resulted in formation of adipocytes (J), smooth muscle cells (K), and chondrocytes (L, M). Scale bars: 50 µm (J), 100 µm (K).

FIG. 3: Differentiation of transient precursors into induced Schwann cells (iSCs). (A-D) iSCs express Schwann cell marker proteins. Scale bars: 50 µm. (E) Efficiency of conversion. Quantification of PLP positive cells at d31. Few PLP positive fibroblasts are due to background signal. Columns show means+/−SD (n=3). Data were analysed using Student's t-test. (F) Principal component analysis of whole transcriptome expression profiles from cells at day 0 (fibroblasts), d7 (early tP), d11 (early tP), d18 (late tP), day 39 (iSCs), and primary Schwann cells (pSCs). Principal component 1 (x-axis) accounts for 27.4% and principal component 2 (y-axis) accounts for 16.5% of the variation of the data set. Each stage is represented by at least two datapoints derived from independent experiments. The clustered transcriptomic profiles at day 39 suggest the robustness of the protocol. (G) Enrichment map of gene-sets (Reactome/RONET) in day 39 (iSCs) versus day 0 (fibroblasts) cells. Red nodes represent gene-sets enriched in iSCs, whilst blue nodes represent gene-sets enriched in fibroblasts. Nodes are grouped and annotated by their similarity according to related gene-sets; shared genes are represented as a green line between nodes. Cluster of functionally related nodes were summarized and annotated using WordCloud. Data from at least two independent assays were analyzed. (H) Whole patch clamp analysis of iSCs. Voltage-dependent current obtained from a −70 mV to +40 mV in 10 mV increasing steps protocol from a holding potential Vh=−80 mV. Absence of early inward current confirms the deficiency of voltage-dependent Na+ channels, while the outward component is consistent with the presence of voltage-dependent K+ channels. (I) Maximal voltage-dependent K+ currents are significantly higher in iSCs than in fibroblasts. Columns show means+/−SD of different cells (FBs: n=12; iSCs: n=7) measured in two independent experiments. Data were analysed using Student's t-test.

FIG. 4: Functionality of iSCs in co-culture with neuronal cells. (A-C) Culture of NSC-derived neurons on POL (A), on cell tracker labeled fibroblasts (B) and iSCs (C), respectively. Scale bars: 100 µm. NSC-neurons cultured with iSCs form a more dense and branched network analyzed by MAP2 stained area (D), neurite number (E), and total neurite length (F). Columns show mean+/−SD (n=3). Data were analysed using Student's t-test. *: $p<0.05$. (G) Co-culture of iSCs with primary rat DRG neurons. Some iSCs form single myelinated fragments (arrowhead) detected by co-localization of MBP staining (yellow) and neurofilament (NF) staining (magenta). Scale bars: 20 µm.

Figure 5D:
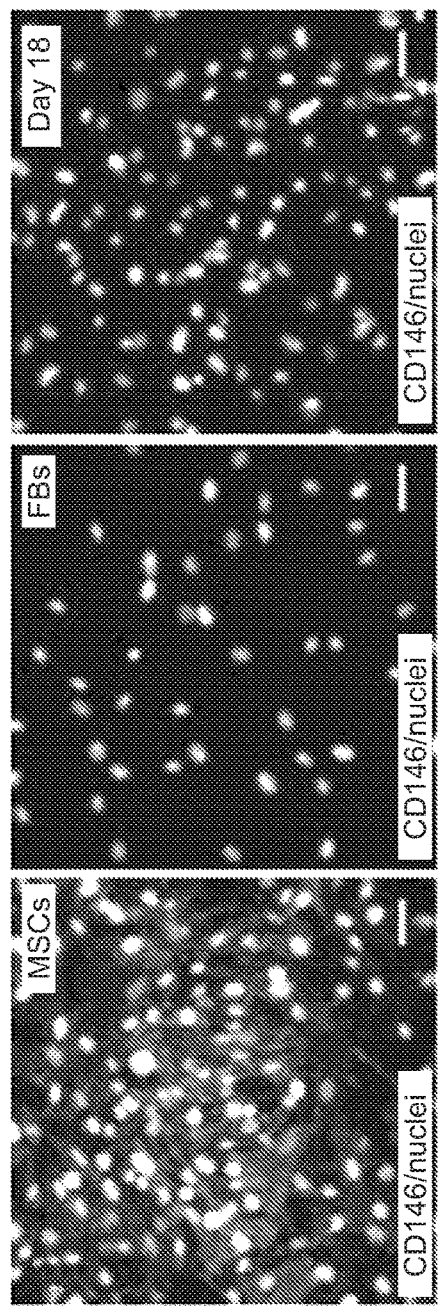
Figure 5E:
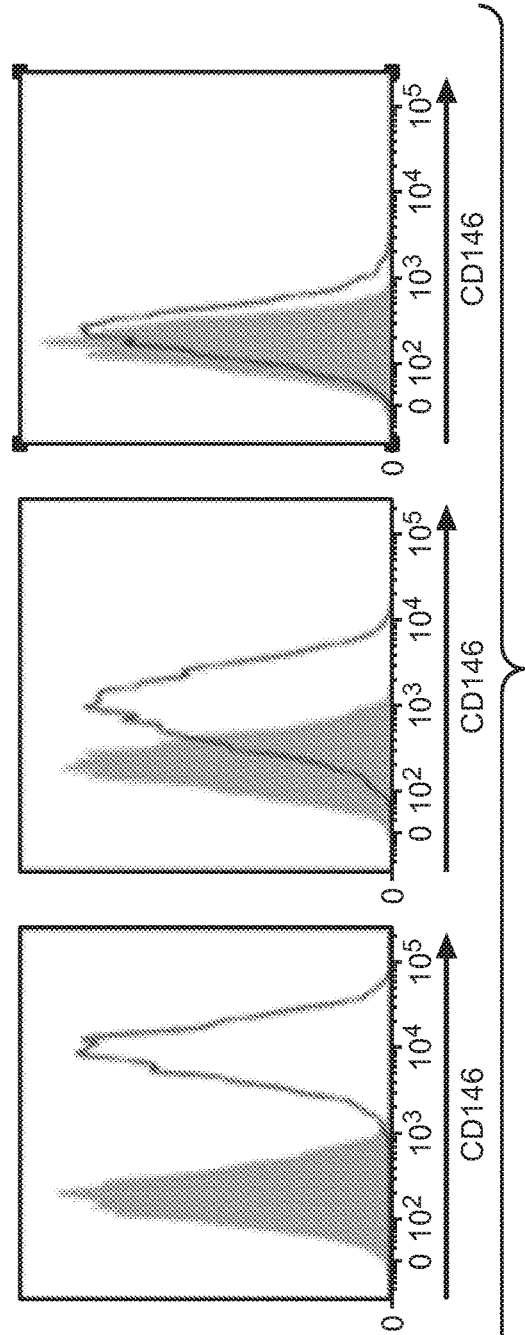

FIG. 5: Characterization of human fibroblasts used for iSC generation. (A-C) Human fibroblasts do not express neural crest or Schwann cell markers. (A) Phase contrast image of fibroblasts. Scale bar: 50 µm. (B) Flow cytometry analysis of fibroblasts showing that initial fibroblast population does not contain cells expressing the neural crest marker CD271. (C) Immunostaining for neural crest and Schwann cell markers. Nuclei were visualized with Hoechst staining. Scale bars: 50 µm. (D, E) Fibroblast cultures and induced transient precursor cells do not contain mesenchymal stem cells (MSCs). Analysis of the MSC marker CD146 by immunostaining (D) and flow cytometry (E). MSCs derived from embryonic stem cells were used as positive control. Scale bars in D: 50 µm.

Figure 6:
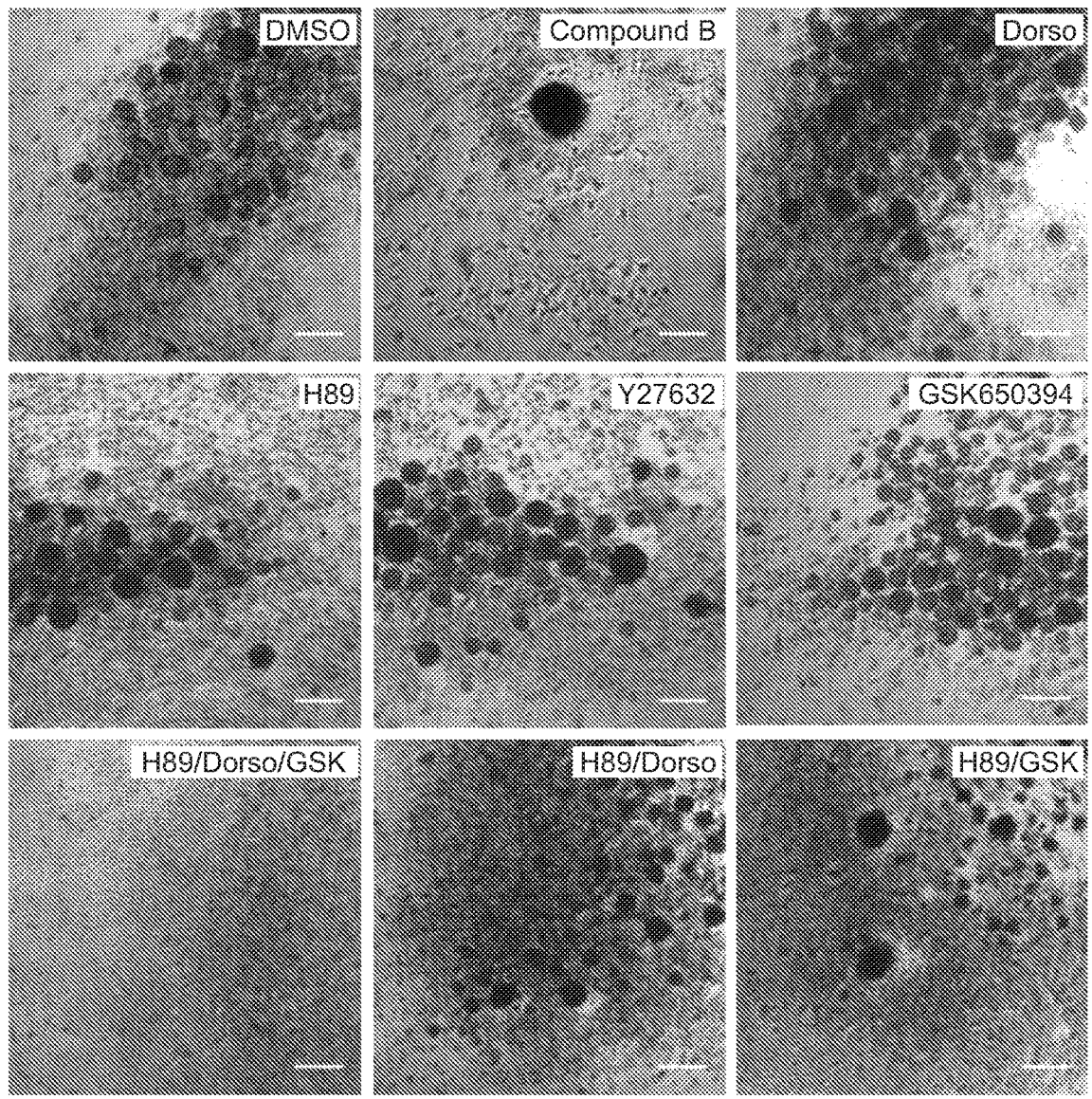
Figure 7B:
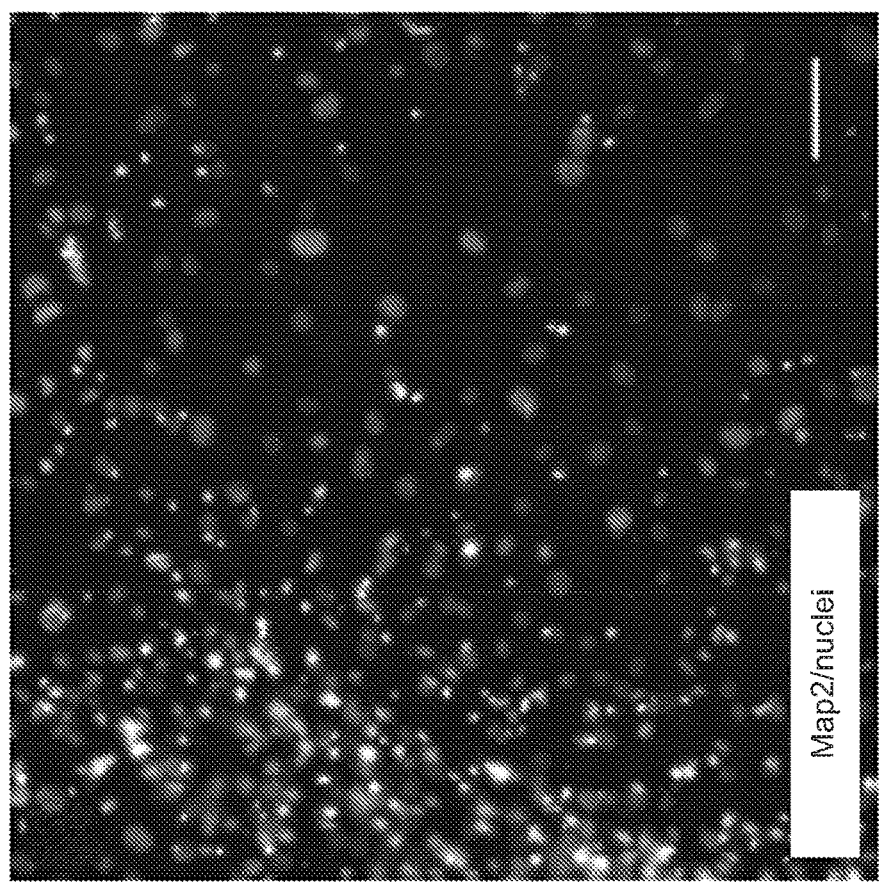
Figure 7A:
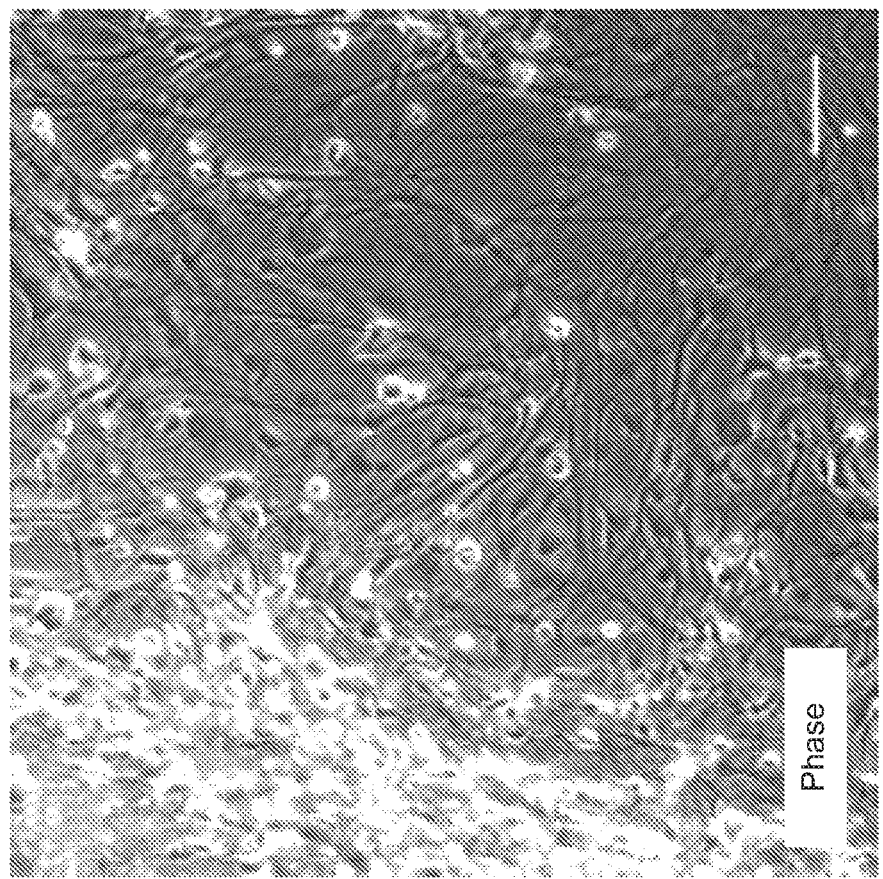
Figure 7C:
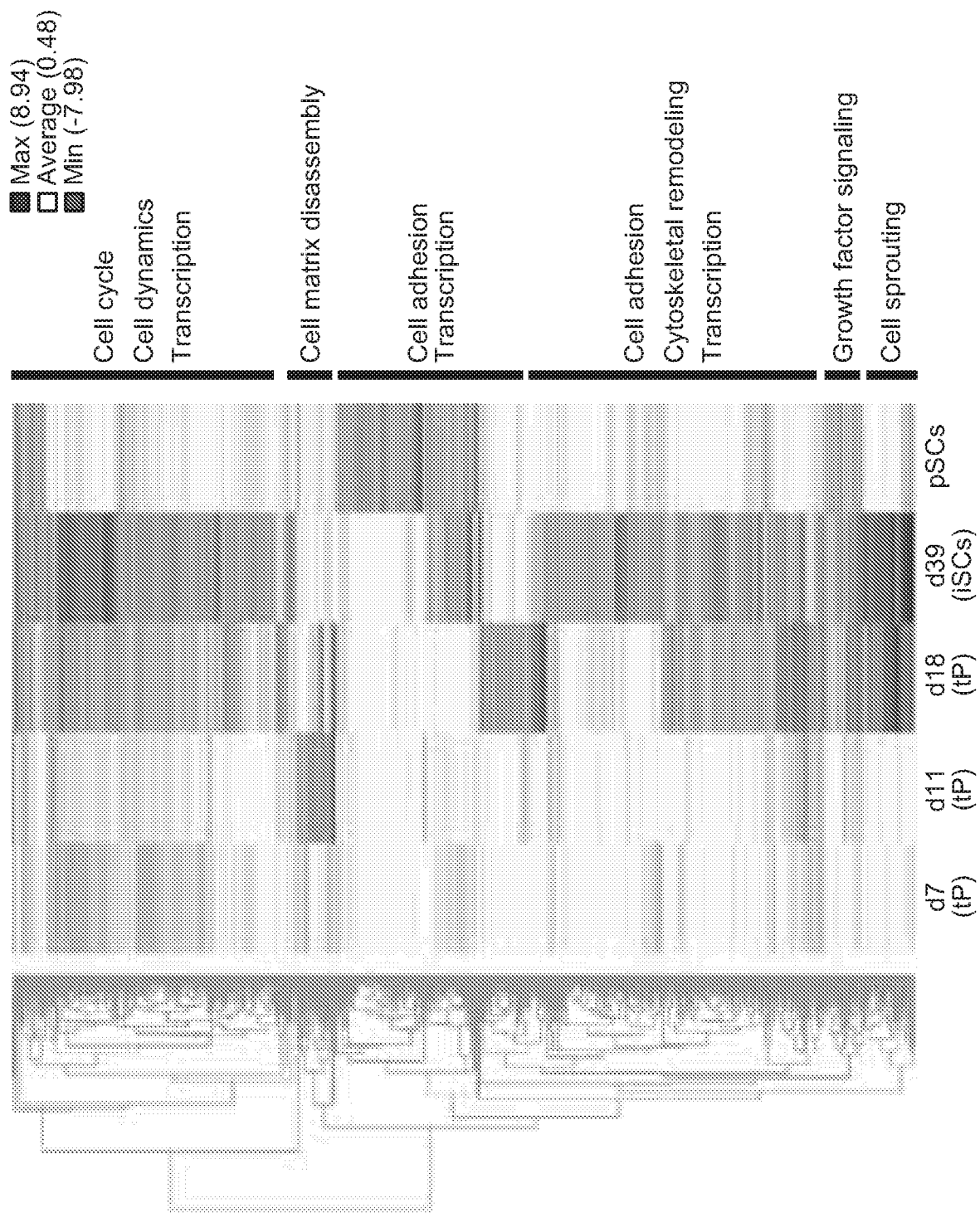
Figure 7D:
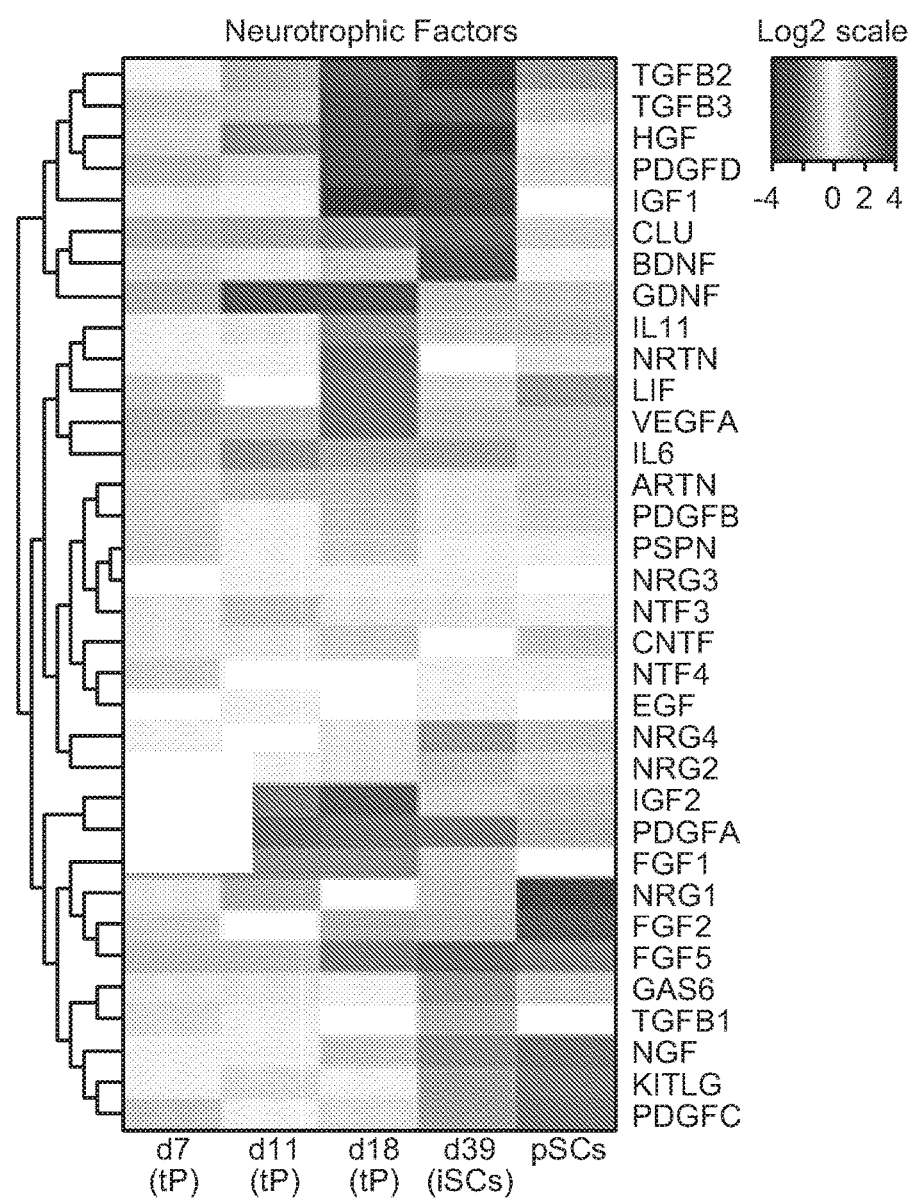

FIG. 6: Attachment of spheres to laminin substrate was mediated by Compound B treatment. Secondary spheres generated with Compound B or inhibitors of single Compound B targets two hours after plating on POL. Only Compound B treated spheres (top middle) have attached and started to migrate. In control (DMSO) and single inhibitor conditions floating spheres have aggregated in center of wells. Scale bars: 200 µm.

FIG. 7: (A, B) Conversion protocol did not yield neurons as shown by negative Map2 staining at day 31. Nuclei were visualized with Hoechst staining. Scale bars: 100 µm. (C, D) Whole gene expression profiles during conversion process. (C) Heat map of the differentially expressed genes (>10 fold change during at least 1 time point) at day 11 (early tP), d18 (late tP), and day 39 (iSCs) relative to day 0 (fibroblasts). Clusters for globally down-regulated genes (blue) and up-regulated genes (red) were generated using average linkage and Euclidean distance. Biological process GO terms were used for cluster annotation. For each stage, data from at least two independent assays were analysed. (D) Heat map showing differential expression of the neurotrophic factors. Log 2 expression ratios indicate down-regulation in blue and up-regulation in red. Data from at least two independent experiments are shown.

Figures 8A, 8B, 8C, 8D, 8E, 8F, 8G, 8H, 8I:
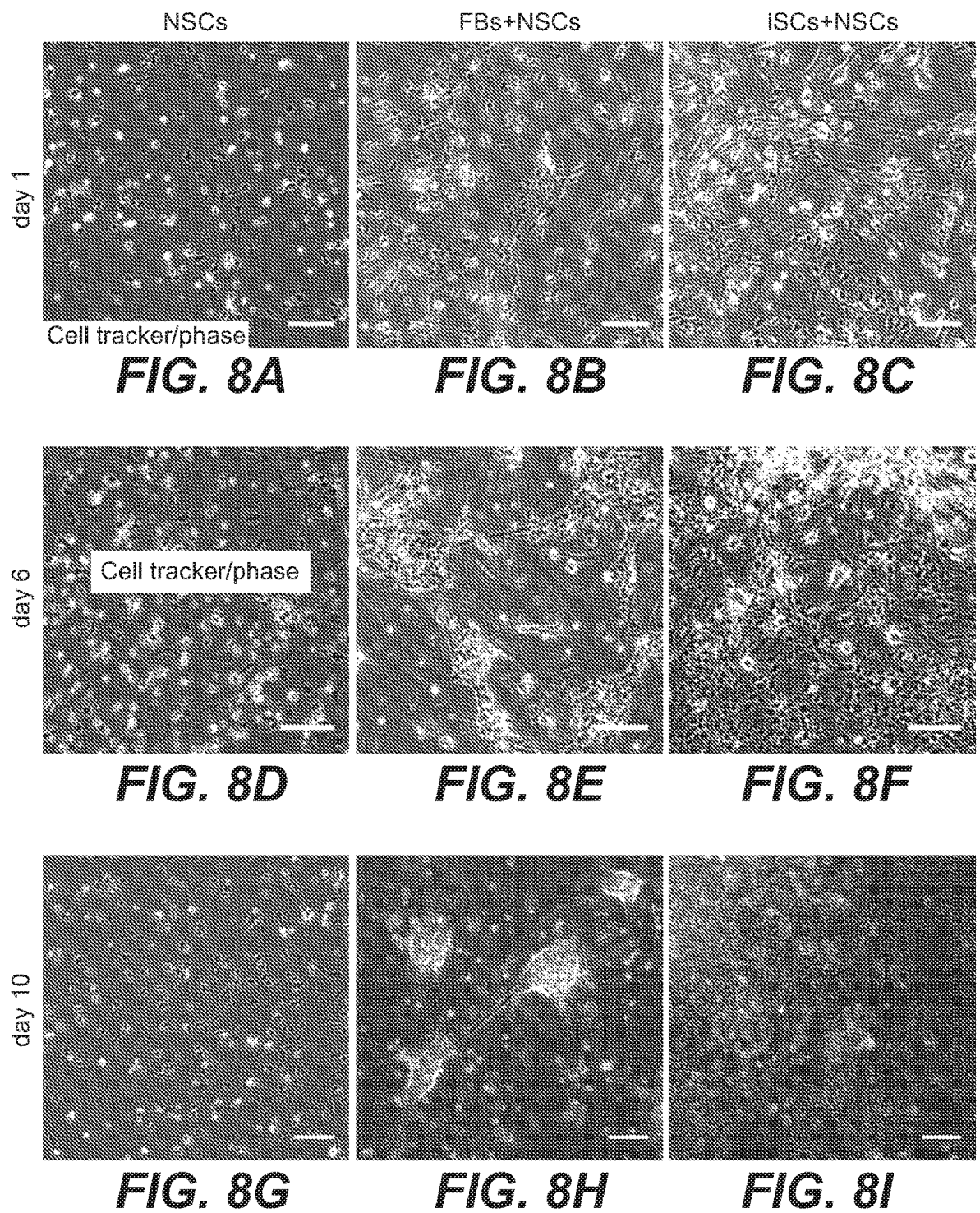

FIG. 8: Time course of co-culture of NSC-derived neurons on POL, cell tracker labeled fibroblasts or cell tracker labeled iSCs. Overlays of phase contrast images and cell tracker signal (red). NSC-neurons can be identified by characteristic small, dark soma. At day 1, NSC-neurons have attached on all three surfaces (A-C). Prolonged co-culture with fibroblasts led to aggregation of neurons and poor neurite outgrowth (E, H). Co-culture with iSCs resulted in proliferation and formation of multicellular network (F, I). Scale bars: 100 µm. J: Co-culture with iSCs led to an increased number of NSC-neurons compared to NSC-neurons grown on POL. Neurons were identified as cell tracker negative cells at day 13 of co-culture. Columns show mean+/−SD of three independent experiments. Data were evaluated using Student's t-test.

DETAILED DESCRIPTION OF THE INVENTION

Current protocols for direct conversion of one cell type into another often suffer from low efficiencies. This might be partially due the fact that many protocols attempt to obtain cell types that are postmitotic, e.g. cardiomyocytes or neurons. Thus, the conversion procedure includes a stop of proliferation which reduces both yield and efficiency. Additionally, non-dividing cells appear to be less amenable to forced phenotypic alterations like reprogramming, possibly due to a less plastic epigenetic landscape. Provided therein is a novel two-step approach to efficiently convert somatic cells like fibroblast into Schwann cells (SCs) without the requirement of genetically modifying the cells by introducing genes. In a first step, the fibroblasts are reprogrammed into neural crest cells (NCCs), a dividing population of SC progenitors. The NCCs can be expanded and then—in a second step—differentiated into mature SCs. In addition to Schwann cells the NCCs can also give rise to chondrocytes, smooth muscle cells or adipocytes.

Neural crest cells are multipotent cells that originate at the border of the neural plate and non-neural ectoderm during embryogenesis and give rise to various cell types e.g. Schwann cells, peripheral neurons, melanocytes, smooth muscle cells, and cartilage. Neural crest specification is a highly complex process that is regulated by numerous signaling cues like for example bone morphogenic protein (BMP), Sonic Hedgehog (Shh), Wnt, Fibroblast growth factor (Fgf), and Notch (Stuhlmiller and Garcia-Castro, 2012). Moreover, specification of neural crest is closely linked to neuroepithelial fate determination. Differentiation of pluripotent stem cells into neural cells in vitro often yields a small proportion of NCCs (Chambers et al., 2009).

The inventors of the present invention found that the combination of neural inductive cues together with NCC specifiers induces a NCC fate in fibroblasts. Surprisingly the inventors found that Compound B (N-{(3R,4R)-4-[4-(2-Fluoro-6-hydroxy-3-methoxy-benzoyl)-benzoylamino]-azepan-3-yl}-4-hydroxy-3,5-dimethyl-benzamide, also referred to as 3,5-Dimethyl-4-hydroxybenzoic acid {(3R,4R)-4-[4-(2-Fluoro-6-hydroxy-3-methoxy-benzoyl)-benzoylamino]-azepan-3-yl}-amide hydrochloride, see e.g. WO03/076429) can induce the reprogramming of somatic cells into neural crest cells. The inventors of the present invention show that this compound selectively promotes proliferation of neural stem cells with no effect on mesenchymal stem cells (FIG. 1A).

Provided herein is a method of Neural Crest cells from somatic cells, comprising:

a) culturing somatic cells in medium supplemented with valproic acid, b) culturing the cells obtained in step (a) in a serum-free medium supplemented with N-{(3R,4R)-4-[4-(2-Fluoro-6-hydroxy-3-methoxy-benzoyl)-benzoyl amino]-azepan-3-yl}-4-hydroxy-3,5-dimethyl-benzamide.

In one embodiment the method does not comprise genetically modifying the somatic cells or the cells obtained in step (a) by the introduction of genes.

Media suitable for culturing the somatic cells in step a) are any known media suitable for growing a certain somatic cell type in a dish. For example fibroblasts are grown in low serum fibroblast medium (e.g. FibroGro, Millipore).

Media suitable for culturing the cells in step b) are any serum-free media, preferably supplemented with one or more growth factors selected from the group of basic fibroblast growth factor (bFGF), epidermal growth factor (EGF), brain derived neutrotrophic factor (BDNF), Heparin, Delta like protein 4 (Dll4), Jagged1, Sonic Hedgehog (SHH), fibroblast growth factor 8 (FGF8).

The term "somatic cell" as used herein refers to any cell forming the body of an organism that are not germ line cells (e.g. sperm and ova, and the cells from which they are made (gametocytes)) and undifferentiated stem cells. Internal organs, skin, bones, blood and connective tissue are all made up of somatic cells. Preferred somatic cells used in the method described herein are fibroblast cells, adipocytes or keratinocytes and are preferably obtained from skin biopsy.

In one embodiment the somatic cells are fibroblasts. Fibroblasts useful therein are for example lung fibroblasts and foreskin fibroblasts.

Preferably, the somatic cells used for conversion into neural crest cells are of mammalian origin, most preferably of human origin. Said human somatic cells can be obtained from a healthy individual or from a patient. Preferably said somatic cells are chosen from the group of fibroblast cells, adipocytes or keratinocytes. These donor cells can be easily obtained from any suitable source. Preferred herein are sources that allow isolation of donor cells without invasive procedures on the human body. Methods for isolating fibroblast cells are well known in the art. Fibroblast cells may be obtained from any suitable source, for example from various organ tissues or skin tissue. Preferred fibroblasts are lung fibroblasts, foreskin fibroblasts, and adult dermal fibroblasts. In a special embodiment of this invention, said human fibroblasts are obtained from a patient, for example by skin biopsy (e.g. Reprogramming of human somatic cells to pluripotency with defined factors. George Q. Daley et al. Nature 2008; A method for the isolation and serial propagation of keratinocytes, endothelial cells, and fibroblasts from a single punch biopsy of human skin, Normand et al. In Vitro Cellular & Developmental Biology—Animal, 1995). Adipocytes and keratinocytes can also be easily derived by skin biopsy or plucked hair (Isolation and cultivation of human keratinocytes from skin or plucked hair for the generation of induced pluripotent stem cells, Belmonte et al. Nature Protocols 2010) and are also preferred donor cells for the method of this invention. Other somatic cells suitable for conversion into neural crest cells are leucocytes cells obtained from blood samples or epithelial cells or other cells obtained from urine samples.

As used herein, "neural crest cells" refers to a subset of multipotent cells which express at least one of the neural markers selected from the group of Sox10, Snail, Twist1, Krox20, CD271, FoxD3, AN2. In one embodiment the neural crest cells obtained by the method disclosed herein express all of the neural markers Sox10, Snail, Twist1, Krox20, CD271, FoxD3, AN2. The neural crest cells obtained by the method described herein are also referred to as "iNCCs": induced neural crest cells. Neural crest cells can be expanded indefinitely and may differentiate into Schwann cells, chondrocytes, smooth muscle cells, and adipocytes.

As used herein, the term "reprogramming" refers to one or more steps needed to convert a somatic cell to a less-differentiated cell, for example for converting fibroblast cells, adipocytes or keratinocytes into neural crest cells. Reprogramming of a somatic cell to a neural crest cell is achieved by the method disclosed therein.

In one embodiment step b) comprises culturing the cells in suspension culture. The suspension culture promotes formation of sphere-like structures and therefore selects for the cells that undergo reprogramming. The term "suspension culture" as used herein refers to the culture of cells such that the cells do not adhere to the solid support or the culture vessel. To transfer cells into a suspension culture, they are for example removed from the culture receptacle by a cell scraper and transferred to sterile low attachment plates containing culture medium, which do not allow adhesion of the cells to the surface of the plate. Thus, the cells are cultured in suspension without adherence to a matrix or the bottom of the dish.

In one embodiment the serum-free medium of step b) is supplemented with an inhibitor of bone morphogenetic protein (BMP). In one embodiment the inhibitor of BMP is noggin (Synonyms: NOG; SYM1; SYNS1).

In one embodiment the serum-free medium of step b) is supplemented with a small molecule inhibitor of Transforming growth factor beta (TGFβ). In one embodiment the inhibitor of TGF β is SB431542 (see. E.g. Laping, N J; Grygielko E, Mathur A, Butter S, Bomberger J, Tweed C, Martin W, Fornwald J, Lehr R, Harling J, Gaster L, Callahan J F, Olson BA (2002). "Inhibition of transforming growth factor (TGF)-beta1-induced extracellular matrix with a novel inhibitor of the TGF-beta type I receptor kinase activity: SB-431542". Molecular Pharmacology 62 (1): 58-64, commercially available e.g. Sigma Prod. No. S 4317).

In one embodiment the serum-free medium of step b) is supplemented with a small molecule inhibitor of glycogen synthase kinase 3 (GSK3β). In one embodiment the inhibitor of GSK3β is 3-(3-Amino-phenyl)-4-(1-methyl-1H-indol-3-yl)-pyrrole-2,5-dione, also referred to as "compound 21" or "CP21" herein; see e.g. L. Gong et al; Bioorganic& Medicinal Chemistry Letters 20 (2010), 1693-1696.

These inhibitors may be used singly or in any combination. Addition of one or more of these inhibitors is optiOnal and improves the process. Reprogramming/conversion of fibroblasts also works with Compound B alone.

In one embodiment, the serum-free medium of step b) is supplemented with inhibitors of BMP, TGF β, and GSK3β. In one embodiment, the serum-free medium of step b) is supplemented with noggin, CP21 and SB431542. In one embodiment, the serum-free medium of step b) is supplemented with 0.1-1 µg/ml noggin, 0.1-5 µM CP21 and 1-50 µM SB431542. In one embodiment, the serum-free medium of step b) is supplemented with 0.5 µg/ml noggin, 1 µM CP21 and 10 µM SB431542.

One embodiment comprises use of N-{(3R,4R)-4-[4-(2-Fluoro-6-hydroxy-3-methoxy-benzoyl)-benzoylamino]-azepan-3-yl}-4-hydroxy-3,5-dimethyl-benzamide in a method for producing neural crest cells from somatic cells.

One embodiment comprises use of 3-(3-Amino-phenyl)-4-(1-methyl-1H-indol-3-yl)-pyrrole-2,5-dione in a method for producing neural crest cells from somatic cells.

In one embodiment step a) comprises culturing the cells for 2 days.

In one embodiment step b) comprises culturing the cells for 7 to 14 days. In one embodiment step b) comprises culturing the cells for 7 days. In one embodiment step b) comprises culturing the cells for 14 days.

In one embodiment the somatic cells are human cells.

One preferred aspect of the present invention is a method for generating patient specific neural crest cells. Hence, in one embodiment the somatic cells are obtained from a subject suffering from a neurological disease.

"Neurological disease" as used herein is defined as a disorder of the nervous system, and include disorders that involve the central nervous system (brain, brainstem and cerebellum), the peripheral nervous system (including cranial nerves), and the autonomic nervous system (parts of which are located in both central and peripheral nervous system). In particular neurological disease includes any disease wherein the function of neural crest cells or Schwann cells is impaired, altered or disrupted. Examples of neurological diseases connected with Schwann cells are Demyelinating diseases, Multiple sclerosis, Myelopathies, Experimental allergic encephalomyelitis (EAE), acute disseminated encephalomyelitis (ADEM), postinfectious or postvaccinal encephalomyelitis, peripheral neuropathies, Schwannomatosis, Charcot-Marie-Tooth disease, Guillain-Barre Syndrome, Chronic inflammatory demyelinating polyradiculoneuropathy (CIDP).

Another aspect of the present invention is a method for generating neural crest cells from somatic cells obtained from a healthy individual.

The term "patient specific neural crest cell" refers to neural crest cells obtained from somatic cells of a patient and are also referred to as autologous neural crest cells. "Neural crest cells obtained from a healthy individual" as used herein refers to neural crest cells obtained from somatic cells of an individual that is not suspected to suffer from any disorder or disease.

In another aspect of the invention, a population of neural crest cells produced by any of the foregoing methods is provided. Preferably, the population of neural crest cells is patient specific, i.e. derived from somatic cells obtained from diseased individuals. In another embodiment said population of cells is obtained from a healthy individual. The neural crest cells can be expanded indefinitely. Culturing is easy and well characterized. It is possible to freeze and thaw neural crest cells aliquots reproducibly. Patient derived neural crest cells represent a disease relevant in vitro model to study the pathophysiology of neurological diseases. Conversion of patients specific somatic cells directly to neural crest cells represents an easy accessible and reproducible technology to generate BioBanks of patient specific neural crest cells. Hence in a further preferred aspect of the invention a BioBank comprising patient specific neural crest cells is envisaged. In another embodiment, a BioBank comprising different populations of neural crest cells obtained from healthy individuals is generated. The term "BioBank" as used herein means a library of biological samples taken from different individuals or species. The archived collection of specimen and associated data is intended for research purposes with the aim of addressing neurological diseases like Demyelinating diseases, Multiple sclerosis, Myelopathies, Experimental allergic encephalomyelitis (EAE), acute disseminated encephalomyelitis (ADEM), postinfectious or postvaccinal encephalomyelitis, peripheral neuropathies, Schwannomatosis, Charcot-Marie-Tooth disease, Guillain-Barre Syndrome, Chronic inflammatory demyelinating polyradiculoneuropathy (CIDP).

In one embodiment the method further comprises c) incubating the product of steps b) under conditions suitable for differentiation of the neural crest cells into a differentiated cell selected from the group of Schwann Cell, chondrocyte, smooth muscle cell or adipocyte.

As used herein the term "differentiating", "differentiation" refers to one or more steps to convert a less-differentiated cell into a somatic cell, for example to convert a neural crest cell into Schwann cells, chondrocytes, smooth muscle cells, and adipocytes.

In one embodiment Schwann Cells, chondrocytes, smooth muscle cells or adipocytes obtained by a method according to any of the above embodiments are provided. Preferably, the Schwann Cells, chondrocytes, smooth muscle cells or adipocytes are patient specific, i.e. derived from somatic cells obtained from diseased individuals. In another embodiment said population of cells is obtained from a healthy individual. For example patient derived Schwann cells represent a disease relevant in vitro model to study the pathophysiology of neurological diseases. Conversion of patients specific somatic cells to Schwann Cells, chondrocytes, smooth muscle cells or adipocytes represents an easy accessible and reproducible technology to generate BioBanks of patient specific Schwann Cells, chondrocytes, smooth muscle cells or adipocytes. Hence in a further preferred aspect of the invention a BioBank comprising patient specific Schwann Cells, chondrocytes, smooth muscle cells or adipocytes is envisaged. In another embodiment, a BioBank comprising different populations of Schwann Cells, chondrocytes, smooth muscle cells or adipocytes obtained from healthy individuals is generated. The term "BioBank" as used herein means a library of biological samples taken from different individuals or species. The archived collection of specimen and associated data is intended for research purposes with the aim of addressing diseases, for example neurological diseases like Demyelinating diseases, Multiple sclerosis, Myelopathies, Experimental allergic encephalomyelitis (EAE), acute disseminated encephalomyelitis (ADEM), postinfectious or postvaccinal encephalomyelitis, peripheral neuropathies, Schwannomatosis, Charcot-Marie-Tooth disease, Guillain-Barre Syndrome, Chronic inflammatory demyelinating polyradiculoneuropathy (CIDP).

In a preferred embodiment the neural crest cells, differentiated Schwann Cells, chondrocytes, smooth muscle cells or adipocytes obtained by this method are used as an in vitro model to study the pathophysiology of neurological diseases. For example, the neural crest cells, differentiated Schwann Cells, chondrocytes, smooth muscle cells or adipocytes obtained by the method of the invention can be used for screening for compounds that reverse, inhibit or prevent neurological diseases. In addition they can be used for screening for compounds that reverse, inhibit or prevent neural side effects of medicaments, for example diabetes medicaments. Preferably, said neural crest cells, differentiated Schwann Cells, chondrocytes, smooth muscle cells or adipocytes obtained by the method of the invention described herein are derived from diseased subjects.

In another embodiment the neural crest cells, differentiated Schwann Cells, chondrocytes, smooth muscle cells or adipocytes obtained by this method are used for screening and evaluating new targets and compounds for treatment of neurological diseases. Preferably, the neural crest cells, differentiated Schwann Cells, chondrocytes, smooth muscle cells or adipocytes obtained by this method are derived from individuals affected by neurological diseases. Differentiating neural crest cells, differentiated Schwann Cells, chondrocytes, smooth muscle cells or adipocytes from diseased subjects represents a unique opportunity to early evaluate drug safety in a human background paradigm. In another embodiment the differentiated Schwann Cells obtained by this method are used as an in vitro model of the peripheral nervous system.

In another aspect, the invention provides a therapeutic composition comprising cells produced by any of the foregoing methods or containing any of the foregoing cell populations. Preferably, the therapeutic compositions further comprise a physiologically compatible solution including, for example, artificial cerebrospinal fluid or phosphate-buffered saline. Said therapeutic composition can be used to treat, prevent, or stabilize a neurological disease such as for example, Demyelinating diseases, Multiple sclerosis, Myelopathies, Experimental allergic encephalomyelitis (EAE), acute disseminated encephalomyelitis (ADEM), postinfectious or postvaccinal encephalomyelitis, peripheral neuropathies, Schwannomatosis, Charcot-Marie-Tooth disease, Guillain-Barre Syndrome, Chronic inflammatory demyelinating polyradiculoneuropathy (CIDP). For example, fibroblast cells, keratinocytes or adipocytes may be obtained by skin biopsy from the individual in need of treatment or from a healthy individual and reprogrammed to neural crest cells, differentiated Schwann Cells, chondrocytes, smooth muscle cells or adipocytes by the method of the invention. In one embodiment of the invention the neural crest cells, differentiated Schwann Cells, chondrocytes, smooth muscle cells or adipocytes obtained by this method are harvested and introduced into the individual to treat the condition. In another embodiment the neural crest cells, obtained by this method are cultured under conditions suitable for differentiation into differentiated Schwann Cells, chondrocytes, smooth muscle cells or adipocytes prior to introduction into the individual, and may be used to replace or assist the normal function of diseased or damaged tissue. The great advantage of the present invention is that it provides an essentially limitless supply of patient specific human neural crest cells, differentiated Schwann Cells, chondrocytes, smooth muscle cells or adipocytes or compatible neural crest cells, differentiated Schwann Cells, chondrocytes, smooth muscle cells or adipocytes from healthy individuals with the same HLA type suitable for transplantation. The use of autologous and/or compatible cells in cell therapy offers a major advantage over the use of non-autologous cells, which are likely to be subject to immunological rejection. In contrast, autologous cells are unlikely to elicit significant immunological responses.

Another embodiment of the invention is the use of biobanks of human neural crest cells, differentiated Schwann Cells, chondrocytes, smooth muscle cells or adipocytes for therapy of neurological diseases. The biobanks preferably comprise human neural crest cells, differentiated Schwann Cells, chondrocytes, smooth muscle cells or adipocytes obtained from patients or healthy individuals with several HLA types. Transplanting cells obtained from a healthy donor to an individual in need of treatment with a compatible HLA type obviates the significant problem of rejection reactions normally associated with heterologous cell transplants. Conventionally, rejection is prevented or reduced by the administration of immunosuppressants or anti-rejection drugs such as cyclosporin. However, such drugs have significant adverse side-effects, e.g., immunosuppression, carcinogenic properties, kidney toxicity as well as being very expensive. The present invention should eliminate, or at least greatly reduce, the need for anti-rejection drugs, such as cyclosporine, imulan, FK-506, glucocorticoids, and rapamycin, and derivatives thereof.

With respect to the therapeutic methods of the invention, it is not intended that the administration of neural crest cells, differentiated Schwann Cells, chondrocytes, smooth muscle cells or adipocytes to a mammal be limited to a particular mode of administration, dosage, or frequency of dosing; the present invention contemplates all modes of administration, including intramuscular, intravenous, intraarticular, intralesional, subcutaneous, or any other route sufficient to provide a dose adequate to prevent or treat a disease. The human neural crest cells, differentiated Schwann Cells, chondrocytes, smooth muscle cells or adipocytes may be administered to the mammal in a single dose or multiple doses. When multiple doses are administered, the doses may be separated from one another by, for example, one week, one month, one year, or ten years. One or more growth factors, hormones, interleukins, cytokines, small molecules or other cells may also be administered before, during, or after administration of the cells to further bias them towards a particular cell type.

Any of the above embodiments may be present singly or in combination.

The term "stem cell" as used herein refers to a cell that has the ability for self-renewal. An "undifferentiated stem cell" as used herein refers to a stem cell that has the ability to differentiate into a diverse range of cell types. As used herein, "pluripotent stem cells" as used herein refers to a stem cell that can give rise to cells of multiple cell types. Pluripotent stem cells (PSCs) include human embryonic stem cells (hESCs) and human induced pluripotent stem cells (hiPSCs). Human induced pluripotent stem cells can be derived from reprogrammed somatic cells, e.g. by transduction of four defined factors (Sox2, Oct4, Klf4, c-Myc) by methods known in the art.

Exemplary Embodiments

1. A method of producing Neural Crest cells from somatic cells, comprising:
   a) culturing somatic cells in medium supplemented with valproic acid,
   b) culturing the cells obtained in step (a) in a serum-free medium supplemented with N-{(3R,4R)-4-[4-(2-Fluoro-6-hydroxy-3-methoxy-benzoyl)-benzoyl amino]-azepan-3-yl}-4-hydroxy-3,5-dimethyl-benzamide.
2. The method of embodiment 1, wherein the method does not comprise genetically modifying the somatic cells or the cells obtained in step (a) by the introduction of genes.
3. The method of embodiment 1 or 2, wherein step b) comprises culturing the cells in suspension culture.
4. The method of any one of embodiments 1 to 3, wherein the serum-free medium of step b) is supplemented with an inhibitor of bone morphogenetic protein (BMP).
5. The method of embodiment 4, wherein the inhibitor of BM' is noggin.
6. The method of any one of embodiments 1 to 5, wherein the serum-free medium of step b) is supplemented with a small molecule inhibitor of Transforming growth factor beta (TGF β).
7. The method of embodiment 6, wherein the small molecule inhibitor of TGF β is SB431542.
8. The method of any one of embodiments 1 to 7, wherein the serum-free medium of step b) is supplemented with a small molecule inhibitor of glycogen synthase kinase 3 (GSK3β).
9. The method of embodiment 8, wherein the inhibitor of GSK3β is 3-(3-Amino-phenyl)-4-(1-methyl-1H-indol-3-yl)-pyrrole-2,5-dione.
10. The method of any one of embodiments 1 to 9, wherein step a) comprises culturing the cells for 2 days.
11. The method of any one of embodiments 1 to 10, wherein step b) comprises culturing the cells for 7 days.
12. The method of any one of embodiments 1 to 11, wherein the somatic cells are fibroblasts.
13. The method of any one of embodiments 1 to 12, wherein the somatic cells are human cells.
14. The method of any one of embodiments 1 to 13, wherein the somatic cells are obtained from a subject suffering from a neurological disease.
15. Neural Crest cells obtained by a method according to any of the preceding embodimentS.
16. The method of any one of embodiments 1 to 14, further comprising
   c) incubating the product of steps b) under conditions suitable for differentiation of the neural crest cells into a differentiated cell selected from the group of Schwann Cell, chondrocyte, smooth muscle cell or adipocyte.
17. Schwann Cells, chondrocytes, smooth muscle cells or adipocytes obtained by a method according to embodiment 16.
18. A biobank of Neural Crest cells according to embodiment 15 or differentiated Schwann Cells, chondrocytes, smooth muscle cells or adipocytes according to embodiment 17.
19. Use of the cells according to embodiment 15 or 17 or of the biobank of embodiment 18 as in vitro model for neurological diseases.
20. A therapeutic composition comprising cells according to embodiment 15 or 17 or the biobank of embodiment 18.

21. Use of N-{(3R,4R)-4-[4-(2-Fluoro-6-hydroxy-3-methoxy-benzoyl)-benzoylamino]-azepan-3-yl}-4-hydroxy-3,5-dimethyl-benzamide in a method for producing neural crest cells from somatic cells.
22. Use of 3-(3-Amino-phenyl)-4-(1-methyl-1H-indol-3-yl)-pyrrole-2,5-dione in a method for producing neural crest cells from somatic cells.
23. The methods and uses essentially as herein described.

Examples

Fibroblast Culture and iSC Conversion

SCC058 foreskin fibroblasts (Millipore) were cultured at 37° C. and 5% $CO_2$ in low serum FibroGro (Millipore). For conversion, 7300 cells/cm² were seeded in fibroblast medium containing 1 mM Valproic acid (VPA, Sigma). Then, cells were treated for two days with 1 mM VPA, and 6 µg/ml polybrene (Millipore) and subsequently transferred to low attachment plates in NSC medium for sphere formation. NSC medium consisted of NeuroCult NS-A proliferation medium (StemCell Technologies) supplemented with Penicillin/streptomycin, bFGF (20 ng/ml), EGF (20 ng/ml), BDNF (20 ng/ml), Heparin (2 µg/ml), D114 (500 ng/ml), Jagged1 (500 ng/ml), SHH (500 ng/ml, peprotech), Ascorbic Acid (0.2 mM, Sigma), FGF8a (100 ng/ml), 10% NSC-CM (medium conditioned by ESC-NSCs), and Compound B (2 µM, Roche).

Compound B has been described e.g. in WO03/076429 and has the following structure:

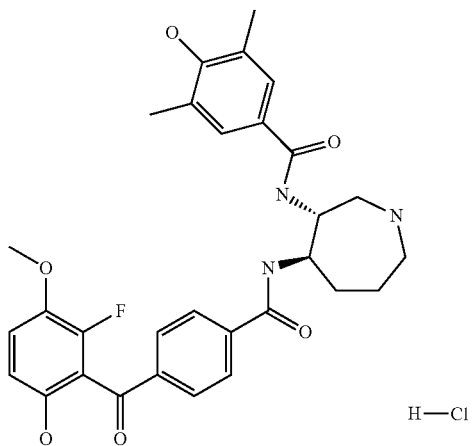 [SMILES: COc1ccc(O)c(C(=O)c2ccc(C(=O)N[C@@H]3CCCNC[C@H]3NC(=O)c3cc(C)c(O)c(C)c3)cc2)c1F ; Cl]

Melting PT (° C.): 180-183° C.
Systematic Name:
[3R,4R]-N-{4-[4-(2-Fluoro-6-hydroxy-3-methoxy-benzoyl)-benzoyl amino]-azep+an-3-yl}-4-hydroxy-3,5-dimethyl-benzamide hydrochlorid All growth factors were from R&D systems if not indicated otherwise. To compare effects of other inhibitors, Compound B was replaced by 2 µM Dorsomorphin, 10 uM H89 (Tocris), 10 µM Y27632, or 10 µM GSK650394 (Tocris), respectively.

After four days, spheres were dissociated with Accutase and single cells were seeded in low attachment plates in NSC medium supplemented with inhibitor mix comprising 500 ng/ml Noggin (peprotech), 10 µM SB431452 (Tocris), and 1 µM CP21 (Roche).

CP21 is a novel, highly selective GSK3β inhibitor: Systematic name 3-(3-Amino-phenyl)-4-(1-methyl-1H-indol-3-yl)-pyrrole-2,5-dione; described in. L. Gong et al; Bioorganic& Medicinal Chemistry Letters 20 (2010), 1693-1696.

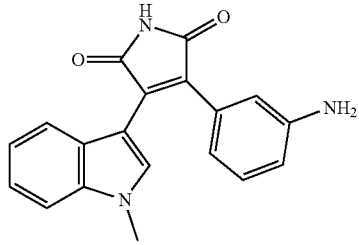

CP21

After 3 days, secondary spheres were seeded on polyornithine-laminin (POL) coated dishes. After attachment (24 hours), medium was replaced with differentiation medium comprising N2B27 (1:1 DMEM/F12 and Neurobasal with beta-mercaptoethanol (50 µM), B27 supplement without vitamin A (1:50, Invitrogen), and N2 supplement (1:100, Invitrogen)) supplemented with antibiotics, BDNF (20 ng/ml), GDNF (20 ng/ml), Laminin (1 m/ml), Ascorbic Acid (0.2 mM) and dibutyryl-cAMP (0.5 mM, Sigma). Every other day, 50% of medium was exchanged. For the first seven days of differentiation, medium was supplemented with the inhibitor mix.

For adipocyte and smooth muscle cell differentiation of neural crest like cells, secondary spheres were plated on growth factor reduced matrigel either as spheres or singularized cells. After 24 hours, medium was changed to adipogenic differentiation medium containing DMEM, 7.5% knockout serum replacement (KOSR, Invitrogen), 0.5% non-essential amino acids, 1% penicillin and streptomycin, 0.1 µM dexamethasone, 10 µg/ml insulin (Sigma) and 0.5 µM rosiglitazone. Medium was changed every other day. After 4 weeks, cells were fixed with 4% PFA and stained with Oilred or antiSMA, respectively. For chondrogenesis, secondary spheres were collected by centrifugation and cultured as pellet in DMEM high glucose supplemented with glutamine, pyruvate, antibiotics, NEAA, 10% FCS, and 10 ng/ml TGF β. After four weeks, pellet was fixed with 4% PFA and analysed by Alcian blue staining.

Embryonic stem cell-derived neural stem cells (ESC-NSCs) were generated as previously described using dual SMAD inhibition protocol (Chambers et al., 2009). NSCs were cultured on POL coated plates at 37° C., 5% $CO_2$ in N2B27 supplemented with bFGF (10 ng/ml), EGF (10 ng/ml), BDNF (20 ng/ml).

For Compound B identification, NSCs were seeded on POL coated plates at 21000 cells/cm² in N2B27. After cell attachment (4 h), compounds were added at indicated concentrations. Negative control cells were treated with DMSO. Cells were incubated for four days and subsequently the amount of ATP was determined using the CellTiterGlo® kit (Promega) according to the manufacturer's instructions.

For iSC/NSC-neuron co-culture, NSCs were cultured in differentiation medium for 13 days. NSC-neurons were detached with Accutase and then seeded in differentiation medium on POL only, fibroblasts or iSCs at 120000 NSC-neurons/12 well. Fibroblasts and iSCs had been previously labeled with CFSE cell tracker (Invitrogen, 10 µM for 20 min). Every other day, 50% of medium was exchanged. Cells were fixed with 4% PFA at day 13 of co-culture.

Kinase Selectivity Profiling

Kinase selectivity profiling was performed using ProfilerPro Kinase Kits from Caliper (PerkinElmer) according to the manufacturer's instructions.

Stainings

For all immunofluorescence stainings, cells were fixed with 4% PFA for 15 min. After blocking with 10% donkey serum, cells were stained with primary antibodies overnight. Subsequently, cells were washed and stained with secondary antibodies conjugated to Alexa 488, 555, and 647 (Molecular Probes). Nuclei were stained with Hoechst (Molecular Probes). Primary antibodies were anti-Sox1 (Santacruz, 1:250), anti-nestin (Millipore, 1:500), anti-Sox10 (Santacruz, 1:200), anti-Snail (Santacruz, 1:100), anti-FoxD3 (Santacruz, 1:100), anti-AN2 (Miltenyi, 1:20), anti-Plp (abcam, 1:75), anti-GalC (Millipore, 1:100), anti-S 100B (abcam, 1:20), anti-MBP (Sigma, 1:100), anti-ABCA2 (santacruz, 1:200), anti-Map2ab (Sigma, 1:800), anti-GFAP (DAKO, 1:500), myelin stain (Molecular probes), and anti-SMA (Dako, 1:100). Cells were imaged using a Zeiss inverted microscope and images were analysed using ImageJ software. Quantifications of Plp and Map2 stainings were performed using an Operetta imaging system and the Harmony image analysis software (PerkinElmer).

For Oilred staining, cells were fixed with 4% PFA for 15 min. After washing with PBS, cells were incubated in Oilred staining solution (0.21% Oilred in 60% isopropanol) at room temperature for one hour. Subsequently, cells were washed 3-5 times with PBS and analysed.

For Alcian blue staining of chondrogenesis, cell pellet was fixed with 4% PFA for 30 min. The pellet was then washed three times with PBS and incubated in Alcian blue staining solution at room temperature overnight. Pellet was destained (20 min room temperature, three times), transferred to PBS and analysed.

Flow Cytometry

At day 18, cells were detached with Accutase and subsequently incubated in conditioned medium at 37° C., 5% CO2 for 2 hours to allow reexpression of surface antigens. Cells were stained for 10 min at 4° C. in MACS running buffer (Miltenyi) containing primary antibodies anti-CD29-PE (BD Bioscience), anti CD271-APC (Miltenyi), or corresponding isotype controls (BD Bioscience), washed with PBS, and then fixed with 2% PFA for 1 hour and stored in PBS at 4° C. Flow cytometry was performed using a BD FACS Cantor, and data were analysed with FlowJo software.

Genome-Wide Gene Expression Analysis

For total RNA extraction, cells were homogenized in tubes prefilled with 1.4 mm ceramic beads and QIAzol lysis reagent using a FastPrep-24 instrument (MP Biomedicals) and the Qiagen miRNeasy Mini Kit with DNase treatment (Qiagen). RNA quality assessment and quantification was performed using microfluidic chip analysis on an Agilent 2100 bioanalyzer (Agilent Technologies). On a Biomek FXp workstation (Beckman Coulter), 10 ng of total RNA was reverse transcribed using the NuGen Ovation Pico WTA Systems V2, followed by fragmentation, and 3'-biotin-labeling with the NuGen Encore Biotin module (NuGEN Technologies). 4.4 µg fragmented cDNA were hybridized for 16 h at 45° C. and 65 rpm on an Affymetrix HG-U133_plus_2 microarray followed by washing, staining, and scanning on a GeneChip Fluidics 450 station and a GeneChip Scanner 3000 (Affymetrix). Affymetrix probe intensities were subjected to robust multi-array analysis (RMA), background correction with quantile normalization, and a median polish probeset summarization as implemented in the Partek Genomics Suite 6.6 software (Partek). Gene names for the probesets were identified using Partek and NetAffyx (Affymetrix). Gene Set Enrichment Analysis was applied to the data on the basis of the BROAD Institute algorithm. Biological processes and signaling pathways were identified using GO term and Reactome/RONET based gene sets. The Cytoscape plug-in enrichment map was used to visualize GSEA results passing significance thresholds (p-value <0.005, False Discovery Rate <0.1). Gene expression heat maps were generated using Tibco Spotfire 3.1.0 (Tibco Software).

Results

Figure 1B:
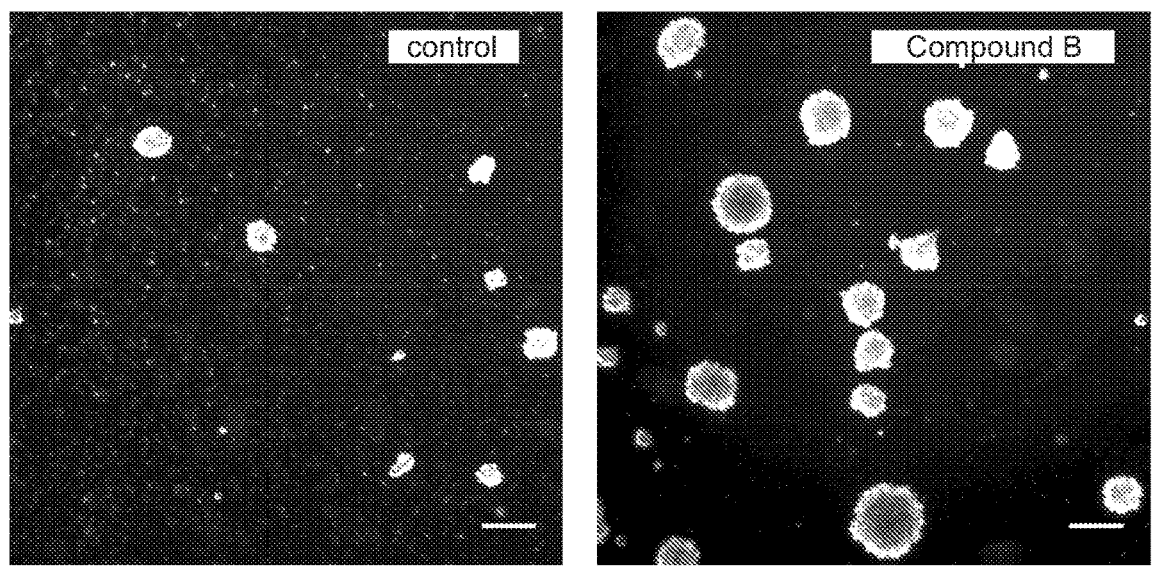
Figure 1C:
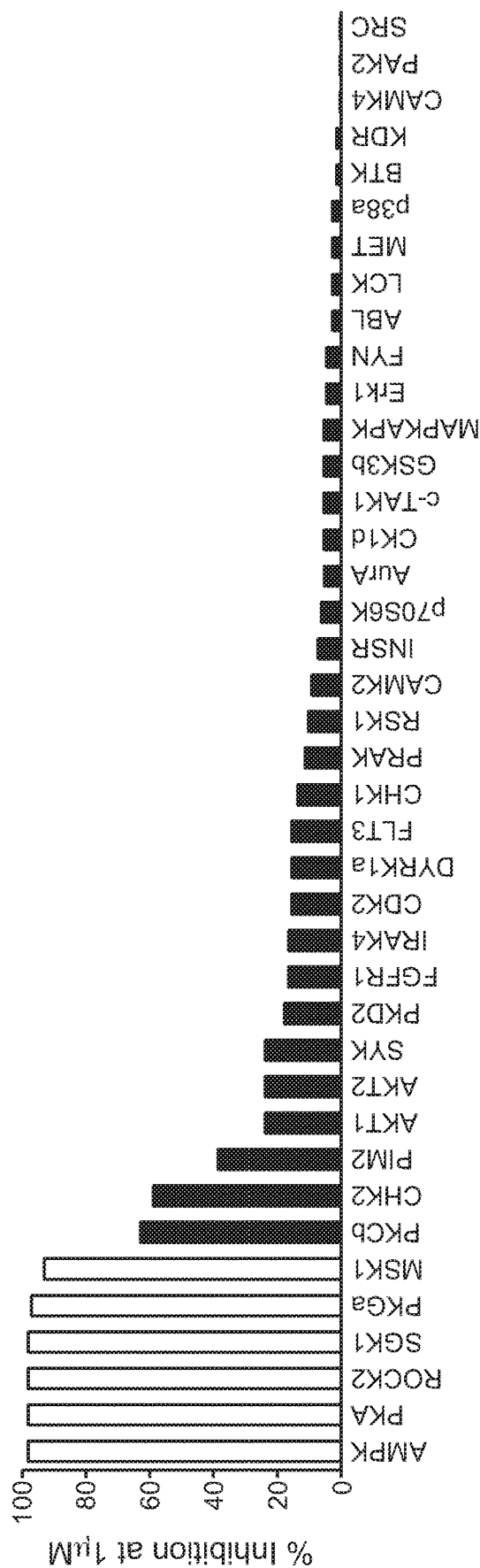
Figure 1D:
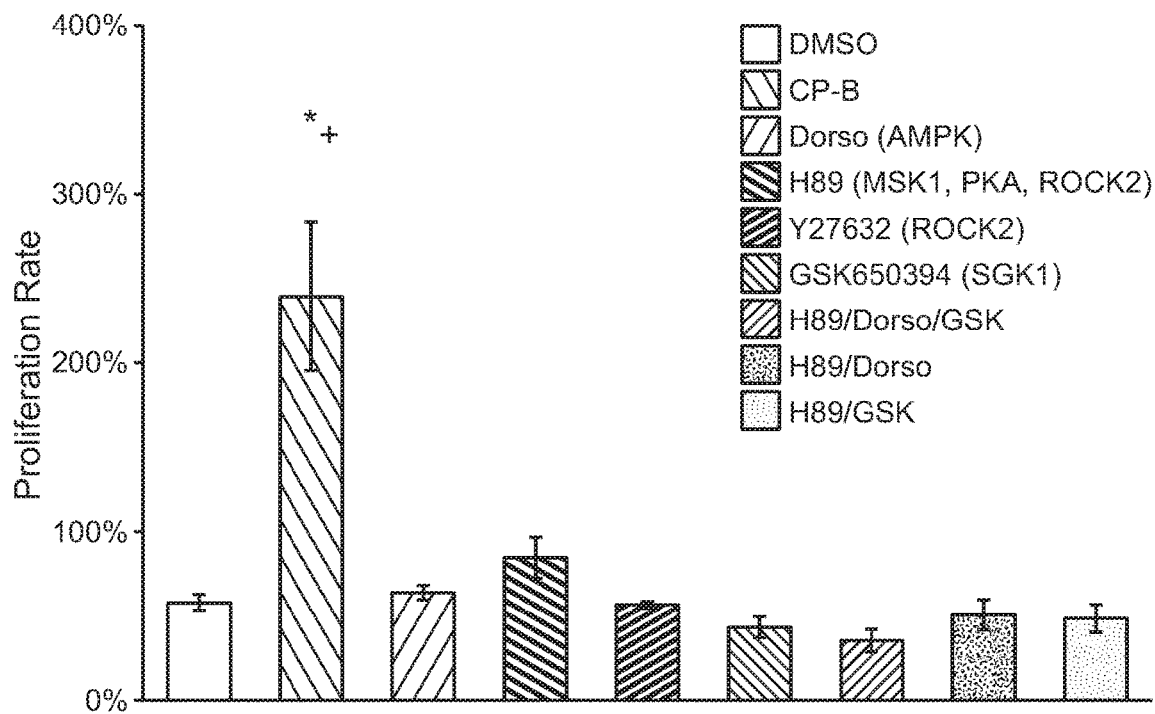
Figure 1D:
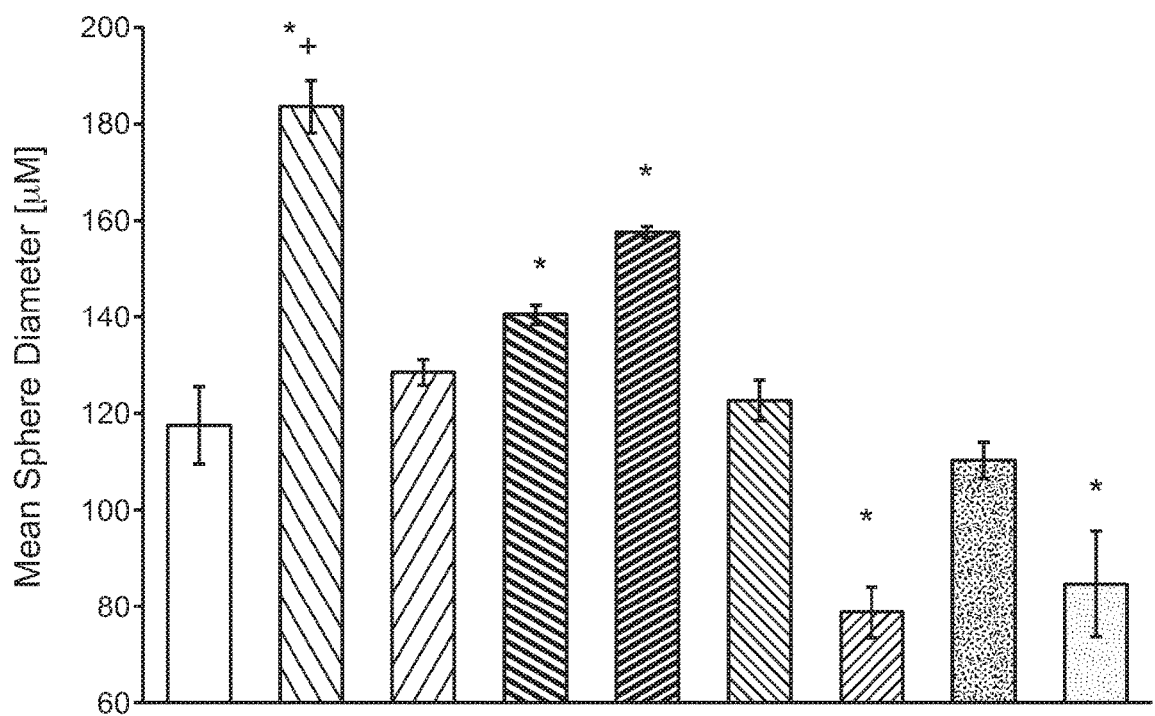
Figure 1E:
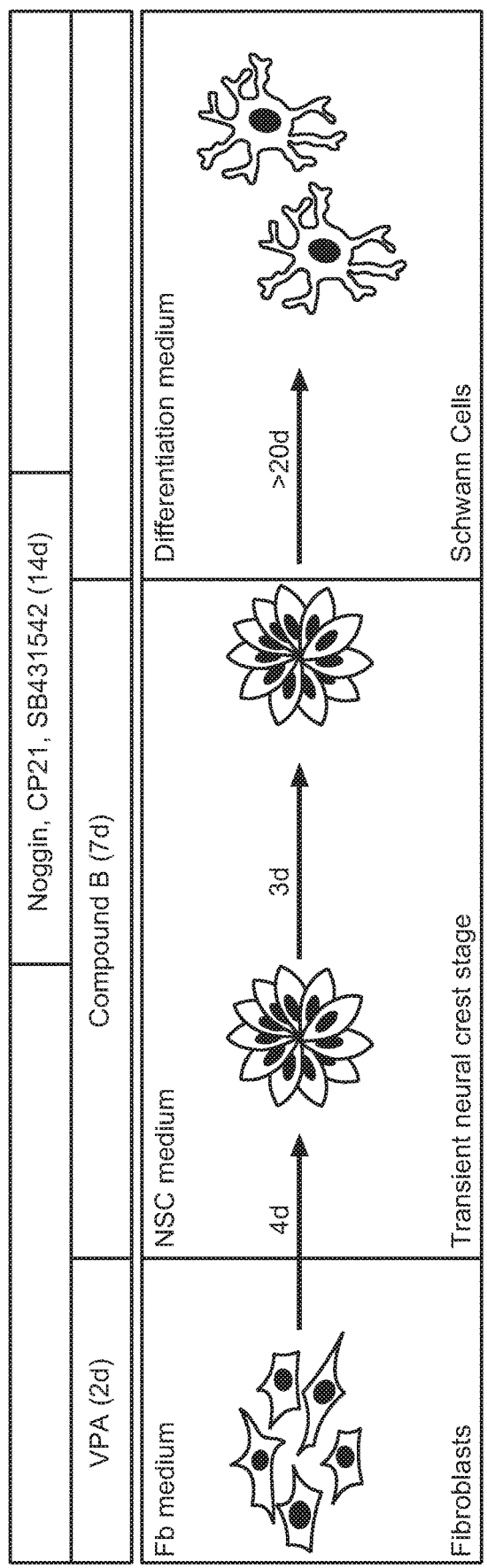
Figure 3F:
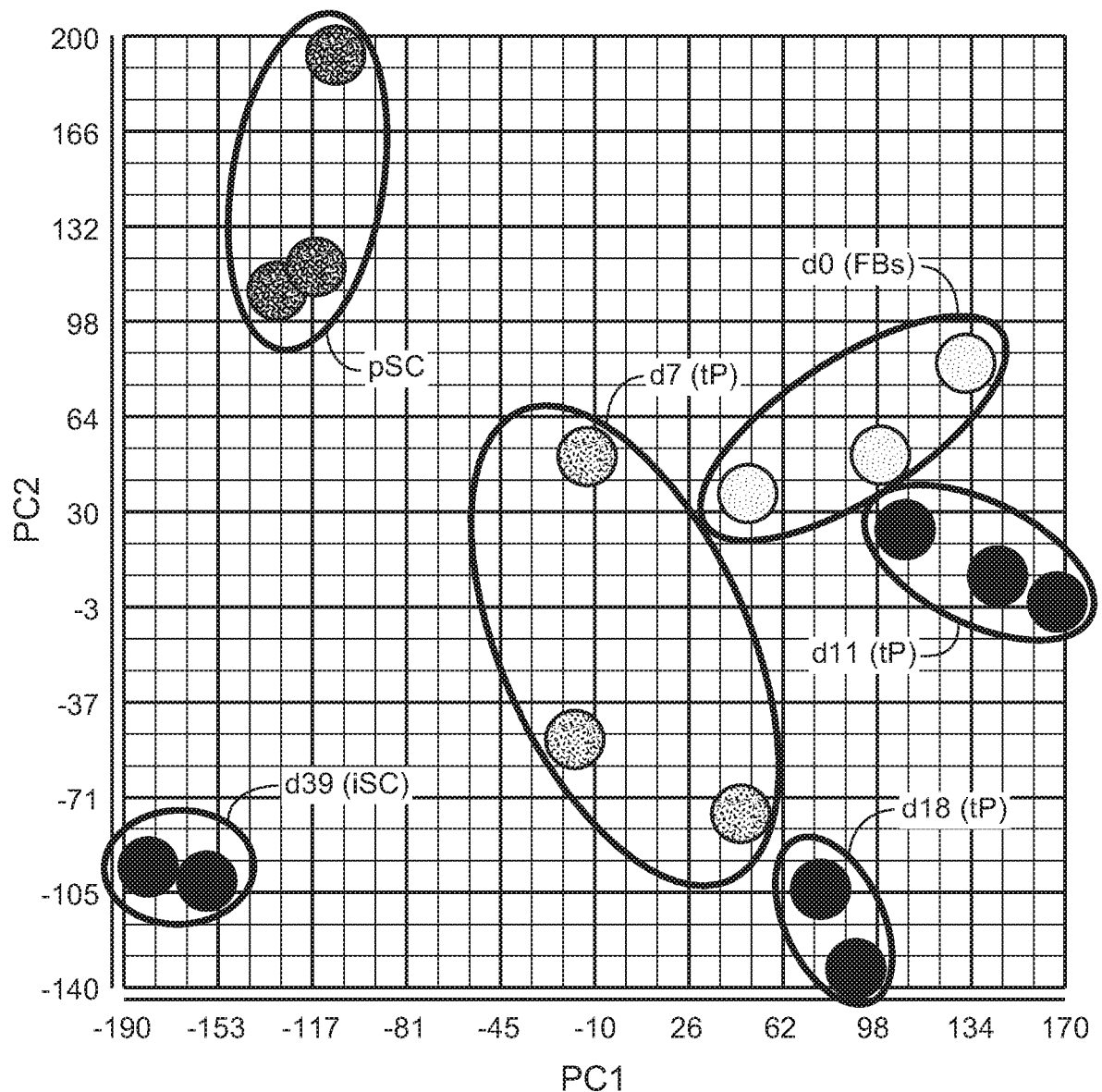
Figure 3G:
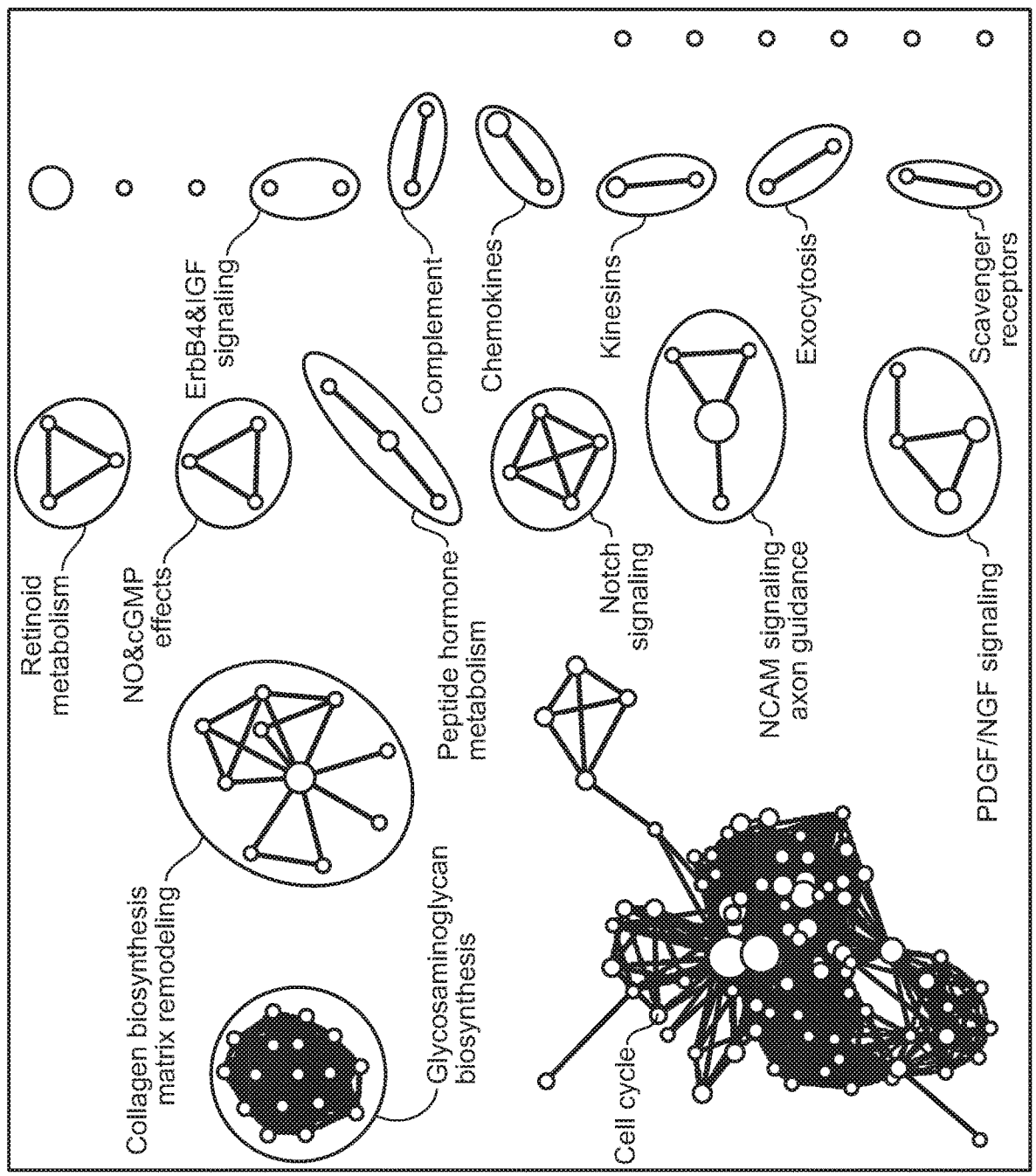
Figure 3H:
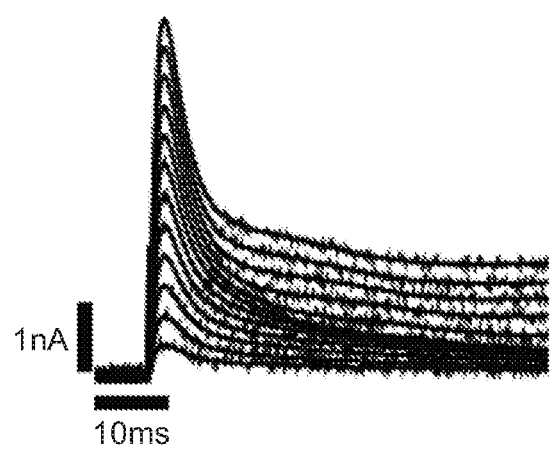
Figure 3I:
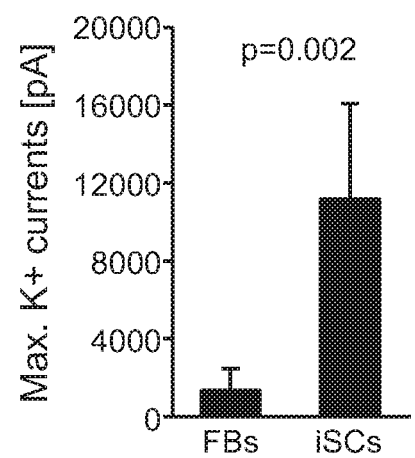

Compound B was shown to selectively promote proliferation of neural stem cells with no effect on mesenchymal stem cells (FIG. 1A). To analyze the capacity of Compound B to induce a NC progenitor stage in fibroblasts, a sphere formation assay was performed. This assay has been used in numerous studies to identify and select cells with stem cell features from various tissues (Dontu et al., 2003; Seaberg et al., 2004; Toma et al., 2001; Tropepe, 2000). Compound B treatment resulted in a significant increase in both sphere size and total cell number (FIG. 1B). Kinase profiling (FIG. 1C) identified Compound B as an efficient multikinase inhibitor with the major targets AMPK, PKA, MSK1, SGK1, ROCK2, and PKGa (inhibition over 80 percent). To test if increased sphere formation capacity upon Compound B treatment was mediated by inhibition of one of these targets or a combination, the effect of specific single kinase inhibitors on sphere formation was tested. Only Compound B treatment resulted in a significant increase in total cell number in suspension culture. Moreover, the average sphere size was also largest upon Compound B treatment (FIG. 1D). Interestingly, combinations of single kinase inhibitors did not result in increased cell numbers as Compound B and sphere size was even slightly reduced compared to controls.

Based on sphere formation as initial step, an optimized protocol to induce a NCC phenotype in fibroblasts (FIG. 1E) was establishd. In brief, treatment with the HDAC inhibitor VPA was followed by the induction of NCC fate by treatment with Compound B in defined neural stem cell medium. The resulting cells were expanded for one passage in suspension and additionally treated with inhibitors of BMP, TGF-β, and GSK3β signaling, an inhibitor mix known to enhance neural conversion of fibroblasts and to allow differentiation of pluripotent stem cells towards neural crest (Ladewig et al., 2012; Menendez et al., 2011). Then, NCC spheres were plated on polyornithine-laminin coated plates and transferred to a differentiation medium. Sphere attachment was observed within 2 hours after plating and cells soon started to migrate out of spheres. In contrast, when spheres had been generated using specific single kinase inhibitors sphere attachment was highly impaired and no or only poor migration of cells was observed (FIG. 6). During physiological NC development, laminin represents one of the key ECM components mediating migration and survival of NC cells (Bronner-Fraser, 1986; Desban et al., 2006). Thus, the capacity to attach rapidly and migrate on laminin substrate indicates that Compound B treated cells have adopted certain NCC features.

Twenty-four hours after attachment of spheres, cells stained positive for Sox1 and Nestin which are markers for both neural epithelium and neural crest. One week later (d18), neural crest specific markers p75, Sox10, FoxD3, Snail, and An2 were detected indicating further conversion to a NCC phenotype. Moreover, loss of fibroblast identity was indicated by downregulation of the fibroblast surface marker CD29. As NCCs are characterized by their capacity to give rise to various different cell types, we tested the ability of the converted cells to give rise to non-neural cell types that originate from NC. When cultured in specific differentiation media converted cells gave rise to adipocytes (identified by OilRed stain), cartilage (identified by Alcian Blue), and SMA positive smooth muscle cells confirming their multipotent differentiation capacity. In summary, these results suggest that Compound B treatment combined with defined culture conditions is sufficient to induce a neural crest cell like fate in human fibroblasts. We named these cells induced neural crest cells or iNCCs.

Next, we wanted to induce differentiation of iNCCs into mature Schwann cells. Therefore, cells were cultured in a standard neural differentiation medium for 3-4 weeks. After an initial proliferation phase in the first passage as iNCCs, cell numbers decreased about 50 percent and then remained the same until the end of the experiment (FIG. 3). After 3-4 weeks, cells displayed the typical morphology of glia cells with a large stellate soma and numerous long protrusions. More than 60 percent of cells stained positive for the Schwann cell marker Plp (FIG. 3). Additionally, cells expressed Schwann cell marker proteins Krox20, S100b, GFAP, and GalC (FIG. 3). No Map2 positive cells could be detected indicating the absence of neurons in the culture (FIG. 7). Untreated fibroblasts stained negative for all markers (FIG. 5). Thus, one can conclude that the iNCCs further differentiated into Schwann cells. We named these cells induced Schwann cells or iSCs.

To analyze the electrophysiological feature of iSCs whole patch clamp recordings were performed. ISCs were not able to generate action potentials, but displayed very high K+ currents upon depolarization indicating the presence of voltage-dependent K+ channels, a common feature of glia cells. When compared to fibroblasts, K+ currents were significantly higher confirming the conversion process (FIG. 3)

Figure 8J:
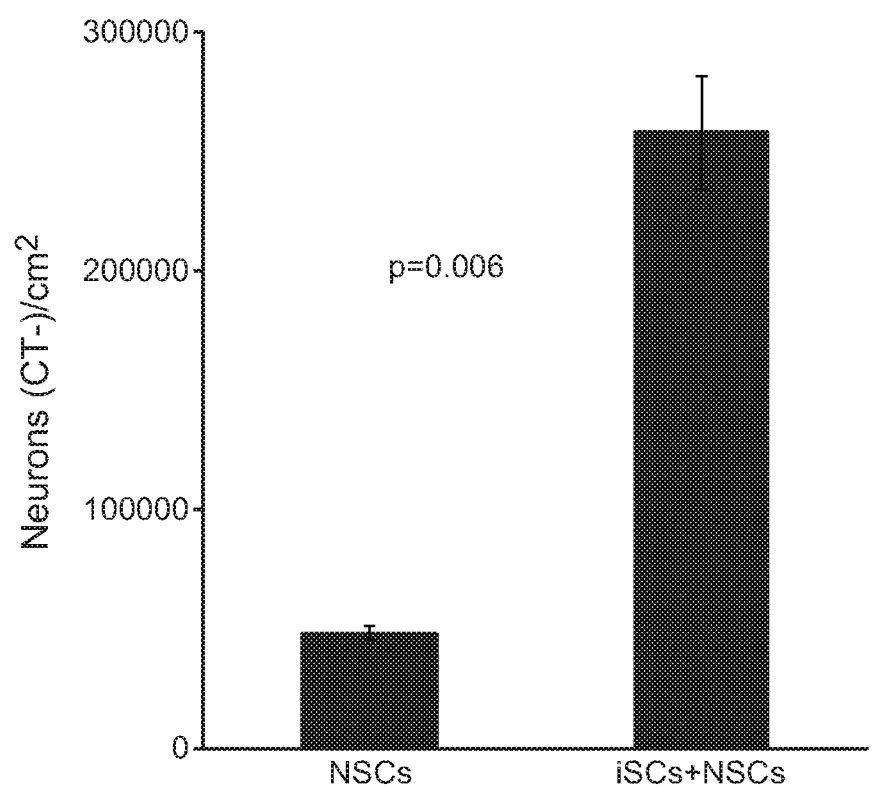

In vivo, Schwann cells fulfill numerous functions to support the growth, differentiation and survival of neuron progenitors and neurons. Additionally, their protrusions form the myelin sheaths insulating one axon from another. To test whether iSCs are able to support neuron differentiation and survival, a co-culture experiment was performed. Human neural stem cells derived from embryonic stem cells were induced to differentiate into neurons (NSC-neurons). After 13 days, NSC-neurons were detached and plated on either poly-ornithine, cell tracker labeled fibroblasts or iSCs. NSC-neurons attached well in all three conditions. NSC-neurons plated on POL continued to differentiate and form a network of neurites. In the first week of co-culture with iSCs, however, a massive increase in NSC-neurons could be observed indicating either increased proliferation or decreased cell death of NSC-neurons. With ongoing co-culture, iSCs and NSC-neurons formed a dense, multicellular network. NSC-neurons plated on fibroblasts, in contrast, did not proliferate and aggregated in dense clusters with only few neurites visible (FIG. 8). Map2 staining at day 13 of co-culture confirmed that NSC-neurons cultured with iSCs formed a larger and more branched neurite network than NSC-neurons grown alone or with fibroblasts (FIG. 4). Image quantification revealed that Map2 positive area as well as number and total length of neurites were significantly increased in the iSC/NSC-neuron co-culture compared to NSC-neurons grown alone (FIG. 4). Moreover, total number of neurons was also increased when cells were co-cultures with iSCs (FIG. 8J). This suggests that iSCs positively affected neuron survival and differentiation. Moreover, co-culture with fibroblasts led to significant decrease in neurite number and length confirming that the beneficial effect of the iSCs is really due to their cellular phenotype and not to their cell type of origin.

Interestingly, we occasionally detected areas where Map2 positive neurites and cell tracker labeled iSC protrusions co-localized, an indication of an ongoing myelination process (FIG. 4).

In summary, iSCs significantly support neuron differentiation and survival and are able to form myelin sheaths, albeit at low frequency. Thus, one can conclude that the conversion process into iSCs also includes the adoption of functional features of physiological Schwann cells.

Discussion

In recent years, numerous studies reporting reprogramming or transdifferentiation of somatic cells have shown that even in terminally differentiated cells a certain plasticity can be evoked and that transition to other unrelated cell types is still possible. This opens new opportunities to obtain cells relevant for clinics or research that are either not or only very difficult to access like e.g. neural cell types. However, current cell conversion protocols in general require the ectopic expression of defined genes. This results in genetic modifications of the reprogrammed cells which might affect later applications in an undesired or unexpected way.

Here, we present a novel approach to transdifferentiate human fibroblasts into mature Schwann cells via a neural crest stage. Importantly, this strategy does not depend on ectopic gene expression but is solely based on chemical modification of defined signaling pathways. We introduce a novel multikinase inhibitor—Compound B—that in combination with defined medium conditions and inhibitors of BMP, TGF-β, and GSK3β enables the conversion of fibroblasts into a neural crest cell stage. These NCCs can then be further differentiated into mature Schwann cells.

Compound B induced the first step of conversion towards a NCC phenotype evaluated by the capacity of sphere formation, proliferation in suspension, and attachment of spheres to laminin. Kinase profiling identified AMPK, MSK1, PKA, ROCK2, PKGa, and SGK1 as main targets of Compound B. Several studies of these signaling pathways allow assumptions regarding the mechanistic regulation of the conversion process. Thus, SGK1 is involved in cellular stress response and its upregulation correlates with occurrence of cell death in neurodegenerative disease (Schoenebeck et al., 2005). In our approach SGK1 inhibition might therefore enhance survival of cells that converted towards a neural fate. AMPK functions as key energy sensor of cells. AMPK activation inhibits IPS generation by preventing transition to a glycolytic metabolism necessary for reprogramming (Vazquez-Martin et al., 2012). Such a metabolic barrier might also be crucial in the current conversion protocol where cells are transferred form serum-containing fibroblast medium to serum-free neural medium. Compound B-mediated AMPK inhibition possibly prevents cellular responses to metabolic stress thus allowing continued glycolysis providing the energy required for the conversion process.

Another Compound B target is the Rho-associated kinase ROCK2. Several studies have shown that this kinase is involved in dissociation-mediated cell death. Its inhibition protects human embryonic stem cells from apoptosis during subcloning or improves human iPS cell generation (Watanabe et al., 2007; Yu et al., 2011). In this conversion strategy, Rock inhibition is probably required to prevent cell death in suspension culture and to allow sphere formation. This idea is supported by the fact, that Rock2 inhibitors H89 and Y27142 also induced an increase in sphere size, albeit not at the same extent as Compound B. Additionally, total cell numbers only increased upon Compound B treatment suggesting that Rock inhibition is sufficient to allow sphere formation, but not cell proliferation. Interestingly, Rock inhibition evokes a proliferative, stem cell-like phenotype in normal and tumor cells from various tissues (Liu et al., 2012b; Terunuma et al., 2010). Furthermore, inhibition of Rock signaling promotes emigration of neural crest cells (Groysman et al., 2008) and has neuroprotective effects (Ding et al., 2009). Thus, additionally to its effect on sphere formation, Rock inhibition probably enhances adoption of features of migrating neural crest cells and promotes survival of these cells.

In summary, Compound B influences the conversion of fibroblasts in two ways. First, it enables transition to a reprogrammable state by preventing stress-induced cell death, allowing sphere formation and providing the required metabolic state. Second, it enhances the adoption of neural crest features which is potentially also mediated by the presence of known NC specifying growth factors like Shh, FGF, and Notch-ligands Jagged and Dll4.

In addition to Compound B treatment the here presented approach includes small molecule-based inhibition of TGF β, BMP, and GSK3β signaling. Modification of these pathways is known to direct differentiation of embryonic stem cells to neuroepitelial and/or neural crest fates (Chambers et al., 2009; Menendez et al., 2011). In combination with Compound B treatment, Tgf-β, BMP, and GSK3β should therefore enhance the conversion towards neural crest. After neural crest specification in vivo, BMP and TGF-β signaling promote non-neural differentiation of neural crest cells into mesenchymal cell types (Chung et al., 2009; John et al., 2011; Shah et al., 1996). Thus, inhibition of these pathways in our protocol also serves the purpose to suppress the formation of these non-neural cells to favor Schwann cell formation.

Nevertheless, the exact mechanisms induced by the chemical treatment and responsible for the conversion towards Schwann cells remain elusive. As forced cellular transdifferentiation is an artificially induced and thus non-physiological process, it is rather difficult to compare it with data from physiological in vivo processes of cell fate determination such as differentiation. This is true not only for the here presented small molecule based conversion but also for transdifferentiation or reprogramming achieved by overexpression of ectopic genes. Both, forced gene expression and small molecule treatments result in activation or repression of key signaling pathways the combination of which leads to the change of cellular identity. In contrast to gene-based approaches, small molecule treatment does not result in genetic modification of the cells. Moreover—and perhaps even more important—treatment with chemical compounds allows a tighter control of the pathway modifications, e.g. by altering concentration of the compound, while gene expression levels are much more difficult to control.

Schwann cells play an important role in development, homeostasis and diseases of the peripheral nervous system (Bhatheja and Field, 2006). Thus far, human Schwann cells can be derived from pluripotent stem cells (Liu et al., 2012a) or as primary cells from peripheral nerve tissue (Casella et al., 1996). While the latter approach only yields a restricted amount of cells, the use of pluripotent stem cells is linked to ethical constraints, potential tumorigenicity and—in case of IPS cells—the introduction of ectopic genes. The chemical conversion of fibroblasts to iSCs represents a novel source for Schwann cells without the involvement of pluripotent stages or genetic modifications. One could hypothesize that iSCs arise from differentiation of rare stem cell populations in the fibroblast culture instead of originating from a real conversion process. Indeed, it has been shown that so called skin derived precursors can be obtained from rodent and human (Toma et al., 2001; Toma et al., 2005). These precursors show NC stem cell properties and can also differentiate into Schwann cells (Fernandes et al., 2004; McKenzie et al., 2006). However, in the beginning of the conversion process cell numbers increased more than 2.5 fold within four days. To reach this proliferation rate, the proportion of stem cells in the initial culture would have to be around 30 percent which is far above reported frequencies for this population in skin (about one percent) (Hunt et al., 2008). Thus, one can conclude that iSCs indeed originated from fibroblasts that converted towards another cellular phenotype. Schwann cell identity of the converted cells was confirmed by glia morphology, expression of numerous Schwann cells markers, electrophysiology, and the ability to efficiently support of neuron differentiation and survival in vitro. Moreover, iSCs appeared to be able of myelinate neurons in vitro, albeit at low frequency. However, this could be due to the subtype of NSC-derived neurons and additional cues that are present during myelination in vivo might be required to achieve the same result in vitro.

Altogether, our work provides a promising new system to generate patient-specific human Schwann cells by pure chemical treatment and without genetic modifications. These cells could represent useful tools to analyse Schwann cell functions or pathophysiology in vitro or to develop cellular interaction models in neuron-Schwann cell co-culture systems.

REFERENCES

Bhatheja, K., and Field, J. (2006). Schwann cells: origins and role in axonal maintenance and regeneration. Int J Biochem Cell Biol 38, 1995-1999.

Bronner-Fraser, M. (1986). An antibody to a receptor for fibronectin and laminin perturbs cranial neural crest development in vivo. Dev Biol 117, 528-536.

Casella, G. T., Bunge, R. P., and Wood, P. M. (1996). Improved method for harvesting human Schwann cells from mature peripheral nerve and expansion in vitro. Glia 17, 327-338.

Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nat Biotechnol 27, 275-280.

Chung, I. H., Yamaza, T., Zhao, H., Choung, P. H., Shi, S., and Chai, Y. (2009). Stem cell property of postmigratory cranial neural crest cells and their utility in alveolar bone regeneration and tooth development. Stem Cells 27, 866-877.

Desban, N., Lissitzky, J. C., Rousselle, P., and Duband, J. L. (2006). alpha1beta1-integrin engagement to distinct laminin-1 domains orchestrates spreading, migration and survival of neural crest cells through independent signaling pathways. J Cell Sci 119, 3206-3218.

Ding, J., Yu, J. Z., Li, Q. Y., Wang, X., Lu, C. Z., and Xiao, B. G. (2009). Rho kinase inhibitor Fasudil induces neuroprotection and neurogenesis partially through astrocyte-derived G-CSF. Brain Behav Immun 23, 1083-1088.

Dontu, G., Abdallah, W. M., Foley, J. M., Jackson, K. W., Clarke, M. F., Kawamura, M. J., and Wicha, M. S. (2003). In vitro propagation and transcriptional profiling of human mammary stem/progenitor cells. Genes Dev 17, 1253-1270.

Fernandes, K. J., McKenzie, I. A., Mill, P., Smith, K. M., Akhavan, M., Barnabe-Heider, F., Biernaskie, J., Junek, A., Kobayashi, N. R., Toma, J. G., et al. (2004). A dermal niche for multipotent adult skin-derived precursor cells. Nat Cell Biol 6, 1082-1093.

Groysman, M., Shoval, I., and Kalcheim, C. (2008). A negative modulatory role for rho and rho-associated kinase signaling in delamination of neural crest cells. Neural Dev 3, 27.

Hunt, D. P., Morris, P. N., Sterling, J., Anderson, J. A., Joannides, A., Jahoda, C., Compston, A., and Chandran, S. (2008). A highly enriched niche of precursor cells with neuronal and glial potential within the hair follicle dermal papilla of adult skin. Stem Cells 26, 163-172.

John, N., Cinelli, P., Wegner, M., and Sommer, L. (2011). Transforming growth factor beta-mediated Sox10 suppression controls mesenchymal progenitor generation in neural crest stem cells. Stem Cells 29, 689-699.

Ladewig, J., Mertens, J., Kesavan, J., Doerr, J., Poppe, D., Glaue, F., Herms, S., Wernet, P., Kogler, G., Muller, F. J., et al. (2012). Small molecules enable highly efficient neuronal conversion of human fibroblasts. Nat Methods 9, 575-578.

Li, W., Jiang, K., and Ding, S. (2012). Concise review: A chemical approach to control cell fate and function. Stem Cells 30, 61-68.

Liu, Q., Spusta, S. C., Mi, R., Lassiter, R. N., Stark, M. R., Hoke, A., Rao, M. S., and Zeng, X. (2012a). Human neural crest stem cells derived from human ESCs and induced pluripotent stem cells: induction, maintenance, and differentiation into functional schwann cells. Stem Cells Transl Med 1, 266-278.

Liu, X., Ory, V., Chapman, S., Yuan, H., Albanese, C., Kallakury, B., Timofeeva, O. A., Nealon, C., Dakic, A., Simic, V., et al. (2012b). ROCK inhibitor and feeder cells induce the conditional reprogramming of epithelial cells. Am J Pathol 180, 599-607.

McKenzie, I. A., Biernaskie, J., Toma, J. G., Midha, R., and Miller, F. D. (2006). Skin-derived precursors generate myelinating Schwann cells for the injured and dysmyelinated nervous system. J Neurosci 26, 6651-6660.

Menendez, L., Yatskievych, T. A., Antin, P. B., and Dalton, S. (2011). Wnt signaling and a Smad pathway blockade direct the differentiation of human pluripotent stem cells to multipotent neural crest cells. Proc Natl Acad Sci USA 108, 19240-19245.

Okita, K., Ichisaka, T., and Yamanaka, S. (2007). Generation of germline-competent induced pluripotent stem cells. Nature 448, 313-317.

Schoenebeck, B., Bader, V., Zhu, X. R., Schmitz, B., Lubbert, H., and Stichel, C. C. (2005). Sgk1, a cell survival response in neurodegenerative diseases. Mol Cell Neurosci 30, 249-264.

Seaberg, R. M., Smukler, S. R., Kieffer, T. J., Enikolopov, G., Asghar, Z., Wheeler, M. B., Korbutt, G., and van der Kooy, D. (2004). Clonal identification of multipotent precursors from adult mouse pancreas that generate neural and pancreatic lineages. Nat Biotechnol 22, 1115-1124.

Shah, N. M., Groves, A. K., and Anderson, D. J. (1996). Alternative neural crest cell fates are instructively promoted by TGFbeta superfamily members. Cell 85, 331-343.

Stuhlmiller, T. J., and Garcia-Castro, M. I. (2012). Current perspectives of the signaling pathways directing neural crest induction. Cell Mol Life Sci 69, 3715-3737.

Takahashi, K., and Yamanaka, S. (2006). Induction of pluripotent stem cells from mouse embryonic and adult fibroblast cultures by defined factors. Cell 126, 663-676.

Terunuma, A., Limgala, R. P., Park, C. J., Choudhary, I., and Vogel, J. C. (2010). Efficient procurement of epithelial stem cells from human tissue specimens using a Rho-associated protein kinase inhibitor Y-27632. Tissue Eng Part A 16, 1363-1368.

Toma, J. G., Akhavan, M., Fernandes, K. J., Barnabe-Heider, F., Sadikot, A., Kaplan, D. R., and Miller, F. D. (2001). Isolation of multipotent adult stem cells from the dermis of mammalian skin. Nat Cell Biol 3, 778-784.

Toma, J. G., McKenzie, I. A., Bagli, D., and Miller, F. D. (2005). Isolation and characterization of multipotent skin-derived precursors from human skin. Stem Cells 23, 727-737.

Tropepe, V. (2000). Retinal Stem Cells in the Adult Mammalian Eye. Science 287, 2032-2036.

Vazquez-Martin, A., Vellon, L., Quiros, P. M., Cufi, S., Ruiz de Galarreta, E., Oliveras-Ferraros, C., Martin, A. G., Martin-Castillo, B., Lopez-Otin, C., and Menendez, J. A. (2012). Activation of AMP-activated protein kinase (AMPK) provides a metabolic barrier to reprogramming somatic cells into stem cells. Cell Cycle 11, 974-989.

Vierbuchen, T., and Wernig, M. (2011). Direct lineage conversions: unnatural but useful? Nat Biotechnol 29, 892-907.

Watanabe, K., Ueno, M., Kamiya, D., Nishiyama, A., Matsumura, M., Wataya, T., Takahashi, J. B., Nishikawa, S., Muguruma, K., and Sasai, Y. (2007). A ROCK inhibitor permits survival of dissociated human embryonic stem cells. Nat Biotechnol 25, 681-686.

Yu, J., Chau, K. F., Vodyanik, M. A., Jiang, J., and Jiang, Y. (2011). Efficient feeder-free episomal reprogramming with small molecules. PLoS One 6, e17557.

The invention claimed is:

1. A method of chemically converting fibroblast cells into neural crest cells, comprising:
   a) culturing fibroblast cells in a medium supplemented with valproic acid, and
   b) culturing the cells obtained in step (a) in a serum-free medium supplemented with
   (i) N-{(3R, 4R)-4-[4-(2-Fluoro-6-hydroxy-3-methoxy-benzoyl)-benzoylamino]-azepan-3-yl}-4-hydroxy-3,5-dimethyl-benzamide,
   (ii) an inhibitor of bone morphogenetic protein (BMP),
   (iii) a small molecule inhibitor of Transforming growth factor beta (TGF-β), and
   (iv) a small molecule inhibitor of glycogen synthase kinase 3 (GSK3β),
   thereby chemically converting said somatic cells into neural crest cells,
   wherein said method does not require expression of any ectopic gene.

2. The method of claim 1, wherein step b) comprises culturing the cells in suspension culture.

3. The method of claim 1, wherein the inhibitor of BMP is noggin.

4. The method of claim 1, wherein the small molecule inhibitor of TGF-β is SB431542.

5. The method of claim 1, wherein the inhibitor of GSK3β is 3-(3-Amino-phenyl)-4-(1-methyl-1H-indol-3-yl)-pyrrole-2,5-dione.

6. The method of claim 1, wherein step a) comprises culturing the fibroblast cells for 2 days.

7. The method of claim 1, wherein step b) comprises culturing the cells for 7 days.

8. The method of claim 1, wherein the fibroblast cells are human fibroblast cells.

9. The method of claim 1, wherein the fibroblast cells are obtained from a subject suffering from a neurological disease.

10. The method of claim 1, further comprising
   c) incubating the product of steps b) under conditions suitable for differentiation of the neural crest cells into a differentiated cell selected from the group of Schwann Cell, chondrocyte, smooth muscle cell or adipocyte.

\* \* \* \* \*